United States Patent
Gray

(10) Patent No.: US 11,491,241 B2
(45) Date of Patent: Nov. 8, 2022

(54) OPTIMIZED AGA GENES AND EXPRESSION CASSETTES AND THEIR USE

(71) Applicant: The University of North Carolina at Chapel Hill, Chapel Hill, NC (US)

(72) Inventor: Steven James Gray, Southlake, TX (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 192 days.

(21) Appl. No.: 16/761,290

(22) PCT Filed: Mar. 22, 2018

(86) PCT No.: PCT/US2018/023727
§ 371 (c)(1),
(2) Date: May 4, 2020

(87) PCT Pub. No.: WO2019/094061
PCT Pub. Date: May 16, 2019

(65) Prior Publication Data
US 2021/0330811 A1    Oct. 28, 2021

Related U.S. Application Data

(60) Provisional application No. 62/582,664, filed on Nov. 7, 2017.

(51) Int. Cl.
*C12N 15/11* (2006.01)
*A61K 48/00* (2006.01)
*C12N 15/86* (2006.01)

(52) U.S. Cl.
CPC ........ *A61K 48/005* (2013.01); *A61K 48/0075* (2013.01); *C12N 15/86* (2013.01); *C12N 2750/14143* (2013.01); *C12N 2800/22* (2013.01)

(58) Field of Classification Search
CPC .............. A61K 48/005; A61K 48/0066; A61K 2039/53; C12N 15/52; C12N 15/67
See application file for complete search history.

(56) References Cited

U.S. PATENT DOCUMENTS 6,018,097 A    1/2000  Selden et al.
2019/0241633 A1*  8/2019  Fotin-Mleczek .. A61K 31/7088

FOREIGN PATENT DOCUMENTS

WO    2010/015079        2/2010
WO    2016/081811        5/2016
WO    2017106313 A1      6/2017

OTHER PUBLICATIONS

Peltola et al., Adenovirus-mediated gene transfer results in decreased lysosomal storage in brain and total correction in live of aspartylglucosaminuria (AGU) mouse, Gene Therapy, vol. 5, pp. 1314-1321. (Year: 1998).*
Karumuthil-Melethil et al. Intrathecal administration of AAV/GALC vectors in 10-11-day-old twitcher mice improves survival and is enhanced by bone marrow transplant, Journal of Neuroscience Research, vol. 94, pp. 1138-1151. (Year: 2016).*
International Preliminary Report on Patentability corresponding to International Application No. PCT/US2018/023727 dated May 22, 2020.
Banning et al. "Functional Analysis of the Ser149/Thr149 Variants of Human Aspartylglucosaminidase and Optimization of the Coding Sequence for Protein Production", Int. J. Mol. Sci. 18(4):706 (2017) 13 pages.
Chen X et al. "AAV9-based gene therapy restores enzymatic activity in a mouse model for aspartylglucosaminuria", 21st ESGLD Workshop Sep. 14-17, 2017 (3 pages).
International Search Report and Written Opinion corresponding to International Application No. PCT/US2018/023727 dated Aug. 2, 2018.
Pulicherla et al. "Engineering Liver-detargeted AAV9 Vectors for Cardiac and Musculoskeletal Gene Transfer", The American Society of Gene & Cell Therapy 19(6):1070-1078 (2011).
Chung et al. "Computational codon optimization of synthetic gene for protein expression" BMC Systems Biology, 6(134):1-14(2012).
Extended European Search Report corresponding to European Patent Application No. 18875101.0 (8 pages) (dated Aug. 3, 2021).

* cited by examiner

*Primary Examiner* — Dana H Shin
(74) *Attorney, Agent, or Firm* — Myers Bigel, P.A.

(57) ABSTRACT

This invention relates to polynucleotides comprising optimized aspartylglucosaminidase (AGA) open reading frames and vectors and cells comprising the same. The invention further relates to methods of using the same for delivery of the open reading frame to a cell or a subject and methods for treating aspartylglucosaminuria (AGU) in a subject.

19 Claims, 8 Drawing Sheets

Specification includes a Sequence Listing.

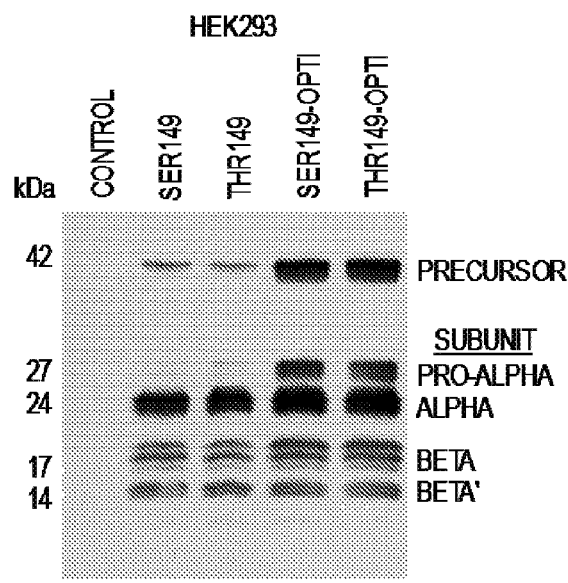
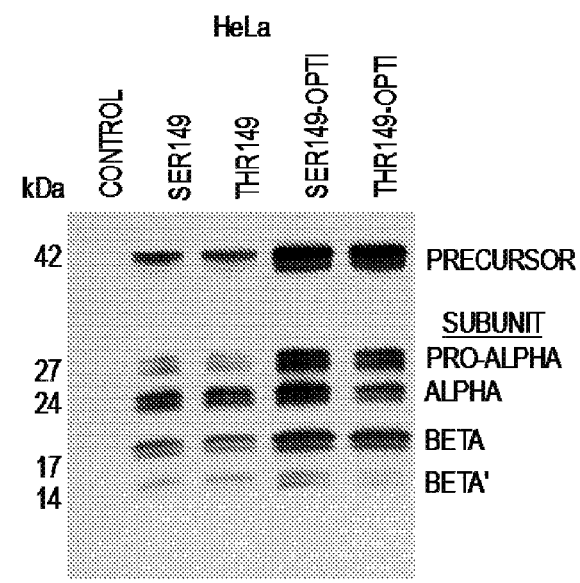
FIG. 9A
FIG. 9B
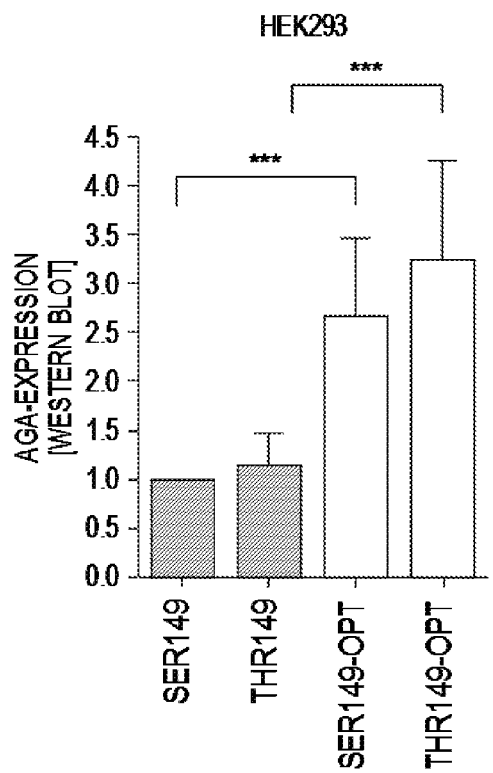
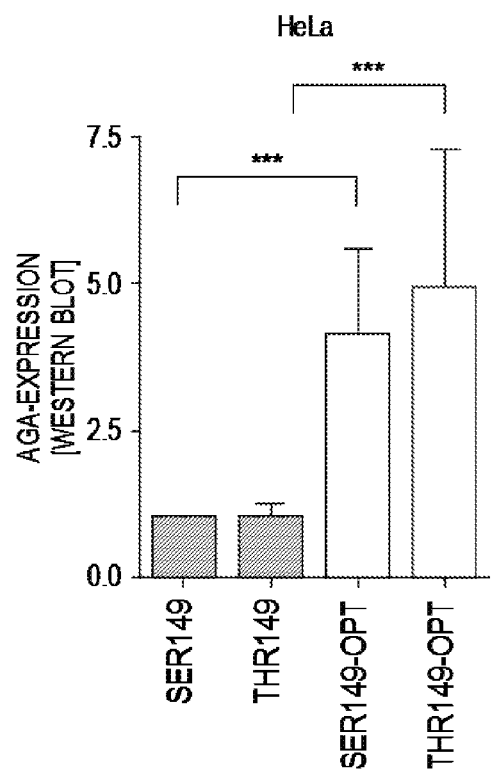
FIG. 9C
FIG. 9D

OPTIMIZED AGA GENES AND EXPRESSION CASSETTES AND THEIR USE

STATEMENT OF PRIORITY

This application is a 35 U.S.C. § 371 national phase application of PCT Application PCT/US2018/023727 filed Mar. 22, 2018, which claims the benefit of U.S. Provisional Patent Application Ser. No. 62/582,664, filed Nov. 7, 2017, the entire contents of each of which are incorporated by reference herein in its entirety.

STATEMENT REGARDING ELECTRONIC FILING OF A SEQUENCE LISTING

A Sequence Listing in ASCII text format, submitted under 37 C.F.R. § 1.821, entitled 5470-805_ST25.txt, 7,029 bytes in size, generated on Apr. 1, 2020 and filed via EFS-Web, is provided in lieu of a paper copy. This Sequence Listing is hereby incorporated by reference into the specification for its disclosures.

FIELD OF THE INVENTION

This invention relates to polynucleotides comprising optimized AGA open reading frame (ORF) sequences, vectors comprising the same, and methods of using the same for delivery of the ORF to a cell or a subject and to treat aspartylglucosaminuria (AGU).

BACKGROUND OF THE INVENTION

Aspartylglucosaminidase (AGA, N4-(β-N-Acetylglucosaminyl)-L-Asparaginase, EC 3.5.1.26) is a lysosomal hydrolase that participates in one of the final steps during the degradation of N-glycosylated proteins. AGA cleaves the bond between N-acetylglucosamine and asparagine after the polypeptide backbone has been degraded. AGA is synthesized as a single-chain precursor molecule that soon after synthesis in the endoplasmic reticulum becomes cleaved into two subunits after dimerization of two precursor molecules. This autocatalytic cleavage takes place between the residues Asp205 and Thr206 and results in the activation of the enzyme. The final active form of AGA is a heterotetramer of two α and two β subunits ($\alpha_2\beta_2$). AGA belongs to the group of so-called N-terminal nucleophile (NTN) hydrolases, as the free α-amino group of Thr206 is involved in the catalysis as the base, whereas the OH group of Thr206 functions as a nucleophile during the catalysis. The members of the NTN hydrolase family, which in addition to AGA also include, e.g., the proteasome β subunit and penicillin acylase, show very little similarity at the amino acid sequence level, but they exhibit a highly similar folded structure.

Mutations in the gene encoding for AGA result in aspartylglucosaminuria (AGU, OMIM 208400), a lysosomal storage disorder that is characterized by progressive mental retardation and some skeletal abnormalities. AGU patients are born seemingly normal, but the progressive course of the disease manifests in, e.g., developmental delay, loss of speech and coarse facial features early in childhood. In adulthood, most AGU patients are severely retarded and require special care. AGU is a rare disease with an unknown prevalence in most populations, but it is enriched in the Finnish population. Due to a founder effect, a specific gene defect designated as $AGU_{Fin-major}$ is found in homozygous form in most Finnish AGU patients, although the parents do not show any consanguinity. The second most common allele in Finland, and also worldwide, is a deletion called $AGU_{Fin-minor}$. Outside Finland, most patients have their individual mutations, either in homozygous form, when originating from consanguineous marriages, or as compound heterozygous mutations.

No treatment is available to cure or slow down the progress of AGU. Bone marrow transplants to replace the missing enzyme have been attempted but the results have been inconclusive. Enzyme replacement therapy has not been feasible as the AGA enzyme is difficult to produce recombinantly due to numerous post-translational modifications, the complex subunit structure, the frequency of dosing, and the inability to cross the blood brain barrier, (Dunder et al., *FASEB J.* 14:361 (2000); Dunder et al., *J. Inhert. Metab. Dis.* 33:611 (2010)).

The present invention overcomes shortcomings in the art by providing optimized AGA genes, expression cassettes, and vectors capable of providing therapeutic levels of AGA expression for treating disorders associated with AGA expression such as AGU.

SUMMARY OF THE INVENTION

The present invention is based, in part, on the development of optimized AGA genes, expression cassettes, and vectors capable of providing therapeutic levels of AGA expression for treating disorders associated with AGA expression such as AGU.

Thus, one aspect of the invention relates to a polynucleotide comprising a human AGA open reading frame, wherein the nucleotide sequence has been codon-optimized for expression in human cells.

A further aspect of the invention relates to an expression cassette comprising a polynucleotide comprising a human AGA open reading frame and vectors, transformed cells, and transgenic animals comprising the polynucleotide of the invention.

Another aspect of the invention relates to a pharmaceutical formulation comprising the polynucleotide, expression cassette, vector, and/or transformed cell of the invention in a pharmaceutically acceptable carrier.

An additional aspect of the invention relates to a method of expressing an AGA open reading frame in a cell, comprising contacting the cell with the polynucleotide, expression cassette, and/or vector of the invention, thereby expressing the AGA open reading frame in the cell.

A further aspect of the invention relates to a method of expressing an AGA open reading frame in a subject, comprising delivering to the subject the polynucleotide, expression cassette, vector, and/or transformed cell of the invention, thereby expressing the AGA open reading frame in the subject.

An additional aspect of the invention relates to a method of treating a disorder associated with aberrant expression of an AGA gene or aberrant activity of an AGA gene product in a subject in need thereof, comprising delivering to the subject a therapeutically effective amount of the polynucleotide, expression cassette, vector, and/or transformed cell of the invention, thereby treating the disorder associated with aberrant expression of the AGA gene in the subject.

Another aspect of the invention relates to a polynucleotide, expression cassette, vector, and/or transformed cell of the invention for use in a method of treating a disorder associated with aberrant expression of an AGA gene or aberrant activity of an AGA gene product in a subject in need thereof.

These and other aspects of the invention are set forth in more detail in the description of the invention below.

BRIEF DESCRIPTION OF THE DRAWINGS

FIGS. 9A-9H show a comparison of processing and activity of optimized and natural AGA variants. SNP149-AGA variants were transiently expressed in (A) HEK293T or (B) HeLa cells. Empty pcDNA3 plasmid served as a control. Western blot with anti-AGA antibody shows correct processing of all constructs, with higher expression level of codon-optimized constructs. (C, D) Western blot signals were quantified and normalized to renilla luciferase activity to correct for transfection efficiency. (E, F) AGA activity was measured in the same cell lysates as used for Western blot. AGA activity was normalized to renilla luciferase activity. (G, H) AGA activity was normalized to AGA protein amount. N=5, shown as mean±SD. Statistical analysis by One-Way Anova.

DETAILED DESCRIPTION OF THE INVENTION

Figure 1:
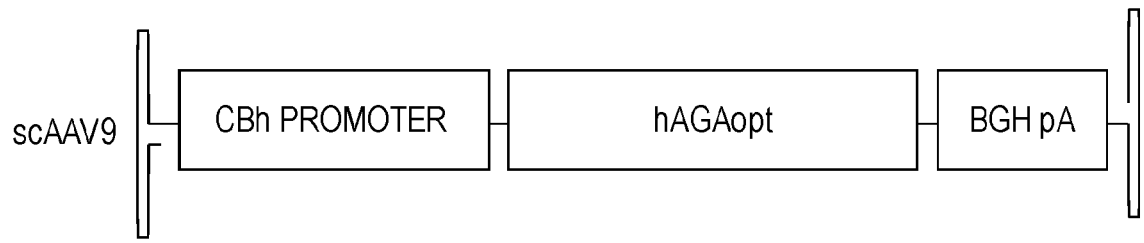
FIG. 1 shows a map of the adeno-associated virus vector of the invention.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. § 1.822 and established usage.

Except as otherwise indicated, standard methods known to those skilled in the art may be used for production of recombinant and synthetic polypeptides, antibodies or antigen-binding fragments thereof, manipulation of nucleic acid sequences, production of transformed cells, the construction of rAAV constructs, modified capsid proteins, packaging vectors expressing the AAV rep and/or cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even ±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence or between the two ends (e.g., between domains) such that the function of the polynucleotide or polypeptide is not materially altered. The total of ten or less additional nucleotides or amino acids includes the total number of additional nucleotides or amino acids added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in biological activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

The term "adeno-associated virus" (AAV) in the context of the present invention includes without limitation AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, and ovine AAV and any other AAV now known or later discovered. See, e.g., BERNARD N. FIELDS et al., VIROLOGY, volume 2, chapter 69 (4th ed., Lippincott-Raven Publishers). A number of additional AAV serotypes and clades have been identified (see, e.g., Gao et al., (2004) *J. Virol.* 78:6381-6388 and Table 1), which are also encompassed by the term "AAV."

The parvovirus particles and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J. Virol.* 71:6823; Chiorini et al., (1999) *J. Virol.* 73:1309; Gao et al., (2002) *Proc. Nat. Acad. Sci. USA* 99:11854; Moris et al., (2004) Virol. 33-:375-383; Mori et al., (2004) Virol. 330: 375; Muramatsu et al., (1996) Virol. 221:208; Ruffing et al., (1994) *J. Gen. Virol.* 75:3385; Rutledge et al., (1998) J. Virol. 72:309; Schmidt et al., (2008) *J. Virol.* 82:8911; Shade et al., (1986) *J. Virol.* 58:921; Srivastava et al., (1983) *J. Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

A "chimeric" AAV nucleic acid capsid coding sequence or AAV capsid protein is one that combines portions of two or more capsid sequences. A "chimeric" AAV virion or particle comprises a chimeric AAV capsid protein.

The term "tropism" as used herein refers to preferential entry of the virus into certain cell or tissue type(s) and/or preferential interaction with the cell surface that facilitates entry into certain cell or tissue types, optionally and preferably followed by expression (e.g., transcription and, optionally, translation) of sequences carried by the viral genome in the cell, e.g., for a recombinant virus, expression of the heterologous nucleotide sequence(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus and/or from a non-integrated episome, as well as any other form which the virus nucleic acid may take within the cell.

The term "tropism profile" refers to the pattern of transduction of one or more target cells, tissues and/or organs. Representative examples of chimeric AAV capsids have a tropism profile characterized by efficient transduction of cells of the CNS with only low transduction of peripheral organs.

TABLE 1

|  | GenBank Accession Number |
|---|---|
| Complete Genomes | |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |

TABLE 1-continued

|  | GenBank Accession Number |
|---|---|
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |

TABLE 1-continued

| | GenBank Accession Number |
|---|---|
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| | |
| Hu14 (AAV9) | AY530579 |
| Hu31 | AY530596 |
| Hu32 | AY530597 |
| Clonal Isolate | |
| | |
| AAV5 | Y18065, AF085716 |
| AAV 3 | NC_001729 |
| AAV 3B | NC_001863 |
| AAV4 | NC_001829 |
| Rh34 | AY243001 |
| Rh33 | AY243002 |
| Rh32 | AY243003 |

The term "disorder associated with aberrant expression of an AGA gene" as used herein refers to a disease, disorder, syndrome, or condition that is caused by or a symptom of decreased or altered expression of the AGA gene in a subject relative to the expression level in a normal subject or in a population.

The term "disorder associated with aberrant activity of an AGA gene product" as used herein refers to a disease, disorder, syndrome, or condition that is caused by or a symptom of decreased or altered activity of the AGA gene product in a subject relative to the activity in a normal subject or in a population.

As used herein, "transduction" of a cell by a virus vector (e.g., an AAV vector) means entry of the vector into the cell and transfer of genetic material into the cell by the incorporation of nucleic acid into the virus vector and subsequent transfer into the cell via the virus vector.

Unless indicated otherwise, "efficient transduction" or "efficient tropism," or similar terms, can be determined by reference to a suitable positive or negative control (e.g., at least about 50%, 60%, 70%, 80%, 85%, 90%, 95% or more of the transduction or tropism, respectively, of a positive control or at least about 110%, 120%, 150%, 200%, 300%, 500%, 1000% or more of the transduction or tropism, respectively, of a negative control).

Similarly, it can be determined if a virus "does not efficiently transduce" or "does not have efficient tropism" for a target tissue, or similar terms, by reference to a suitable control. In particular embodiments, the virus vector does not efficiently transduce (i.e., does not have efficient tropism for) tissues outside the CNS, e.g., liver, kidney, gonads and/or germ cells. In particular embodiments, undesirable transduction of tissue(s) (e.g., liver) is 20% or less, 10% or less, 5% or less, 1% or less, 0.1% or less of the level of transduction of the desired target tissue(s) (e.g., CNS cells).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide," "nucleic acid," or "nucleotide sequence" is a sequence of nucleotide bases, and may be RNA, DNA or DNA-RNA hybrid sequences (including both naturally occurring and non-naturally occurring nucleotide), but is preferably either a single or double stranded DNA sequence.

The term "open reading frame (ORF)," as used herein, refers to the portion of a polynucleotide, e.g., a gene, that encodes a polypeptide.

The term "codon-optimized," as used herein, refers to a gene coding sequence that has been optimized to increase expression by substituting one or more codons normally present in a coding sequence (for example, in a wild-type sequence, including, e.g., a coding sequence for AGA) with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wild-type gene in an otherwise similar cell.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/RE-ADME.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" nucleic acid or nucleotide sequence (e.g., an "isolated DNA" or an "isolated RNA") means a nucleic acid or nucleotide sequence separated or substantially free from at least some of the other components of the naturally occurring organism or virus, for example, the cell or viral structural components or other polypeptides or nucleic acids commonly found associated with the nucleic acid or nucleotide sequence.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder.

As used herein, the term "prevent," "prevents," or "prevention" (and grammatical equivalents thereof) refers to a delay in the onset of a disease or disorder or the lessening of symptoms upon onset of the disease or disorder. The terms are not meant to imply complete abolition of disease and encompasses any type of prophylactic treatment that reduces the incidence of the condition or delays the onset and/or progression of the condition.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

A "heterologous nucleotide sequence" or "heterologous nucleic acid" is a sequence that is not naturally occurring in the virus. Generally, the heterologous nucleic acid or nucleotide sequence comprises an open reading frame that encodes a polypeptide and/or a nontranslated RNA.

As used herein, the term "vector," "virus vector," "delivery vector" (and similar terms) generally refers to a virus particle that functions as a nucleic acid delivery vehicle, and which comprises the viral nucleic acid (i.e., the vector genome) packaged within the virion. Virus vectors according to the present invention comprise a chimeric AAV capsid according to the invention and can package an AAV or rAAV genome or any other nucleic acid including viral nucleic acids. Alternatively, in some contexts, the term "vector," "virus vector," "delivery vector" (and similar terms) may be used to refer to the vector genome (e.g., vDNA) in the absence of the virion and/or to a viral capsid that acts as a transporter to deliver molecules tethered to the capsid or packaged within the capsid.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "recombinant AAV vector genome" or "rAAV genome" is an AAV genome (i.e., vDNA) that comprises at least one inverted terminal repeat (e.g., one, two or three inverted terminal repeats) and one or more heterologous nucleotide sequences. rAAV vectors generally retain the 145 base terminal repeat(s) (TR(s)) in cis to generate virus; however, modified AAV TRs and non-AAV TRs including partially or completely synthetic sequences can also serve this purpose. All other viral sequences are dispensable and may be supplied in trans (Muzyczka, (1992) Curr. Topics Microbiol. Immunol. 158:97). The rAAV vector optionally comprises two TRs (e.g., AAV TRs), which generally will be at the 5' and 3' ends of the heterologous nucleotide sequence(s), but need not be contiguous thereto. The TRs can be the same or different from each other. The vector genome can also contain a single ITR at its 3' or 5' end.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or the SV40 hairpin that serves as the origin of SV40 replication can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV terminal repeat" or "AAV TR" may be from any AAV, including but not limited to serotypes 1, 2, 3, 4, 5, 6, 7, 8, 9, 10 or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The terms "rAAV particle" and "rAAV virion" are used interchangeably here. A "rAAV particle" or "rAAV virion" comprises a rAAV vector genome packaged within an AAV capsid.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) Mol. Therapy 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids.

Naturally occurring, levorotatory (L-) amino acids are shown in Table 2.

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

TABLE 3

Amino Acid Residue Derivatives

| Modified Amino Acid Residue | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |

TABLE 3-continued

Amino Acid Residue Derivatives

| Modified Amino Acid Residue | Abbreviation |
|---|---|
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al., (2006) *Annu. Rev. Biophys. Biomol. Struct.* 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

By "substantially retain" a property, it is meant that at least about 75%, 85%, 90%, 95%, 97%, 98%, 99% or 100% of the property (e.g., activity or other measurable characteristic) is retained.

AGA Expression Cassettes and Vectors

The present invention relates to the design of an AGA expression cassette to provide maximal expression of aspartylglucosaminidase (AGA), the enzyme encoded by the AGA gene, and the use of the expression cassette to achieve therapeutic levels of AGA in a subject.

Thus, one aspect of the invention relates to a polynucleotide comprising a human AGA open reading frame (ORF), wherein the nucleotide sequence has been codon-optimized for expression in human cells. The open reading frame is the portion of the AGA gene that encodes for AGA. As used herein, a human AGA ORF refers to a nucleotide sequence that encodes human AGA. Codon optimization is a technique well known in the art and optimal codons for expression in humans are known. The use of a codon-optimized AGA sequence allows one to distinguish expression of the transduced sequence from expression of the endogenous AGA sequence in a subject.

In some embodiments, the codon-optimized AGA open reading frame encodes an AGA enzyme that is modified from the wild-type sequence, e.g., comprises, consists essentially of or consists of an amino acid sequence in which 1, 2, 3, 4, or 5 residues have been substituted, added, and/or deleted compared to the wild-type amino acid sequence.

In some embodiments, the codon-optimized AGA open reading frame comprises, consists essentially of, or consists of the nucleotide sequence of SEQ ID NO: 1 or a sequence at least about 70% identical thereto, e.g., at least about 70, 75, 80, 85, 90, 91, 92, 93, 94, 95, 96, 97, 98, or 99% identical thereto.

Another aspect of the invention relates to an expression cassette comprising a polynucleotide comprising a human AGA open reading frame. In certain embodiments, the polynucleotide is a human codon-optimized sequence, e.g., a polynucleotide comprising the nucleotide sequence of SEQ ID NO: 1 or a sequence at least about 70% identical thereto, e.g., at least about 70, 75, 80, 85, 90, 91, 92, 93, 94, 95, 96, 97, 98, or 99% identical thereto.

The AGA polynucleotide in the expression cassette may be operably linked to one or more expression elements that may enhance expression of AGA. In some embodiments, the polynucleotide is operably linked to a promoter, e.g., a chicken beta-actin promoter, e.g., a promoter comprising, consisting essentially of, or consisting of the nucleotide sequence of SEQ ID NO: 2 or a sequence at least about 70% identical thereto, e.g., at least about 70, 75, 80, 85, 90, 91, 92, 93, 94, 95, 96, 97, 98, or 99% identical thereto. In some embodiments, the promoter further comprises the chicken beta-actin exon 1 and intron 1, e.g., comprising, consisting essentially of, or consisting of the nucleotide sequence of SEQ ID NO: 3 or a sequence at least about 70% identical thereto, e.g., at least about 70, 75, 80, 85, 90, 91, 92, 93, 94, 95, 96, 97, 98, or 99% identical thereto. This hybrid chicken beta actin promoter advantageously provides robust long-term expression in cells of the central and peripheral nervous systems and is preferred over the commonly used cytomegalovirus promoter, which has been demonstrated to silence gene expression over time (see Gray et al., Human Gene Ther. 22:1143 (2011), incorporated by reference herein in its entirety).

In some embodiments, the polynucleotide is operably linked to an enhancer, e.g., a cytomegalovirus enhancer, e.g., an enhancer comprising, consisting essentially of, or consisting of the nucleotide sequence of SEQ ID NO: 4 or a sequence at least about 70% identical thereto, e.g., at least about 70, 75, 80, 85, 90, 91, 92, 93, 94, 95, 96, 97, 98, or 99% identical thereto.

In some embodiments, the polynucleotide is operably linked to an intron, e.g., a hybrid/modified MVM intron, e.g., an intron comprising, consisting essentially of, or consisting of the nucleotide sequence of SEQ ID NO: 5 or a sequence at least about 70% identical thereto, e.g., at least about 70, 75, 80, 85, 90, 91, 92, 93, 94, 95, 96, 97, 98, or 99% identical thereto. The intron, may be located in any part of the expression cassette where it is effect to enhance expression, e.g., preceding the ORF, within the ORF, or between the ORF and the polyadenylation site.

In some embodiments, the polynucleotide is operably linked to a polyadenylation signal, e.g., a bovine growth hormone polyadenylation signal, e.g., a polyadenylation signal comprising, consisting essentially of, or consisting of the nucleotide sequence of SEQ ID NO: 6 or a sequence at least about 70% identical thereto, e.g., at least about 70, 75, 80, 85, 90, 91, 92, 93, 94, 95, 96, 97, 98, or 99% identical thereto.

Those skilled in the art will further appreciate that a variety of promoter/enhancer elements may be used depending on the level and tissue-specific expression desired. The promoter/enhancer may be constitutive or inducible, depending on the pattern of expression desired. The promoter/enhancer may be native or foreign and can be a natural or a synthetic sequence. By foreign, it is intended that the transcriptional initiation region is not found in the wild-type host into which the transcriptional initiation region is introduced.

Promoter/enhancer elements can be native to the target cell or subject to be treated and/or native to the heterologous nucleic acid sequence. The promoter/enhancer element is generally chosen so that it will function in the target cell(s) of interest. In representative embodiments, the promoter/enhancer element is a mammalian promoter/enhancer element. The promoter/enhance element may be constitutive or inducible.

Inducible expression control elements are generally used in those applications in which it is desirable to provide regulation over expression of the heterologous nucleic acid sequence(s). Inducible promoters/enhancer elements for gene delivery can be tissue-specific or tissue-preferred promoter/enhancer elements, and include muscle specific or preferred (including cardiac, skeletal and/or smooth muscle), neural tissue specific or preferred (including brain-specific), eye (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the AGA ORF is transcribed and then translated in the target cells, specific initiation signals are generally employed for efficient translation of inserted protein coding sequences. These exogenous translational control sequences, which may include the ATG initiation codon and adjacent sequences, can be of a variety of origins, both natural and synthetic.

In certain embodiments, the expression cassette further comprises at least one adeno-associated virus (AAV) inverted terminal repeat (ITR), e.g., two AAV ITRs. The two ITRs may have the same nucleotide sequence or different nucleotide sequences. The AAV ITRs may be from any AAV serotype, e.g., AAV2. Each ITR independently may be the wild-type sequence or a modified sequence. In some embodiments, the expression cassette is an AAV genome, e.g., a self-complementary AAV genome.

In certain embodiments, the expression cassette comprises an enhancer, a promoter, an intron, a human AGA open reading frame, and a polyadenylation site, optionally in the recited order. In certain embodiments, the expression cassette comprises an AAV ITR, an enhancer, a promoter, an intron, a human AGA open reading frame, a polyadenylation site, and an AAV ITR, optionally in the recited order. In certain embodiments, the expression cassette comprises a CMV enhancer, a chicken beta actin promoter, a hybrid/modified MVM intron, a human AGA open reading frame, and a bovine growth hormone polyadenylation site, optionally in the recited order. In certain embodiments, the expression cassette comprises a mutant AAV ITR, a CMV enhancer, a chicken beta actin promoter, a hybrid/modified MVM intron, a human AGA open reading frame, a bovine growth hormone polyadenylation site, and a wild-type AAV ITR, optionally in the recited order.

In some embodiments, the expression cassette comprise, consists essentially of, or consists of the nucleotide sequence of SEQ ID NO: 7 or a sequence at least about 70% identical thereto, e.g., at least about 70, 75, 80, 85, 90, 91, 92, 93, 94, 95, 96, 97, 98, or 99% identical thereto.

A further aspect of the invention relates to a vector comprising the polynucleotide or the expression cassette of the invention. Suitable vectors include, but are not limited to, a plasmid, phage, viral vector (e.g., AAV vector, an adenovirus vector, a herpesvirus vector, an alphavirus, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat). In some embodiments, the vector is a delivery vehicle such as a particle (e.g., a microparticle or nanoparticle) or a liposome to which the expression cassette is attached or in which the expression cassette is embedded. The vector may be any delivery vehicle suitable to carry the expression cassette into a cell.

In some embodiments, the vector is a viral vector, e.g., an AAV vector. The AAV vector may be any AAV serotype, e.g., AAV9. In some embodiments, the AAV vector may comprise wild-type capsid proteins. In other embodiments, the AAV vector may comprise a modified capsid protein with altered tropism compared to a wild-type capsid protein, e.g., a modified capsid protein is liver-detargeted or has enhanced tropism for particular cells.

In some embodiments, the vector is a self-complementary or duplexed AAV (scAAV) vector. scAAV vectors are described in international patent publication WO 01/92551 (the disclosure of which is incorporated herein by reference in its entirety). Use of scAAV to express the AGA ORF may provide an increase in the number of cells transduced, the copy number per transduced cell, or both.

An additional aspect of the invention relates to a transformed cell comprising the polynucleotide, expression cassette, and/or vector of the invention. In some embodiments, the polynucleotide, expression cassette, and/or vector is stably incorporated into the cell genome. The cell may be an in vitro, ex vivo, or in vivo cell.

Another aspect of the invention relates to a transgenic animal comprising the polynucleotide, expression cassette, vector, and/or the transformed cell of the invention. In some embodiments, the animal is a laboratory animal, e.g., a mouse, rat, rabbit, dog, monkey, or non-human primate.

A further aspect of the invention relates to a pharmaceutical formulation comprising the polynucleotide, expression cassette, vector, and/or transformed cell of the invention in a pharmaceutically acceptable carrier.

Methods of Producing Virus Vectors

The present invention further provides methods of producing virus vectors. In one particular embodiment, the present invention provides a method of producing a recombinant AAV particle, comprising providing to a cell permissive for AAV replication: (a) a recombinant AAV template comprising (i) the polynucleotide or expression cassette of the invention, and (ii) an ITR; (b) a polynucleotide comprising Rep coding sequences and Cap coding sequences; under conditions sufficient for the replication and packaging of the recombinant AAV template; whereby recombinant AAV particles are produced in the cell. Conditions sufficient for the replication and packaging of the recombinant AAV template can be, e.g., the presence of AAV sequences sufficient for replication of the AAV template and encapsidation into AAV capsids (e.g., AAV rep sequences and AAV cap sequences) and helper sequences from adenovirus and/or herpesvirus. In particular embodiments, the AAV template comprises two AAV ITR sequences, which are located 5' and 3' to the polynucleotide of the invention, although they need not be directly contiguous thereto.

In some embodiments, the recombinant AAV template comprises an ITR that is not resolved by Rep to make duplexed AAV vectors as described in international patent publication WO 01/92551.

The AAV template and AAV rep and cap sequences are provided under conditions such that virus vector comprising the AAV template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other Ela trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the Ela or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158: 67).

As a further alternative, the rep/cap sequences may be stably incorporated into a cell.

Typically the AAV rep/cap sequences will not be flanked by the TRs, to prevent rescue and/or packaging of these sequences.

The AAV template can be provided to the cell using any method known in the art. For example, the template can be supplied by a non-viral (e.g., plasmid) or viral vector. In particular embodiments, the AAV template is supplied by a herpesvirus or adenovirus vector (e.g., inserted into the Ela or E3 regions of a deleted adenovirus). As another illustration, Palombo et al., (1998) J. Virology 72:5025, describes a baculovirus vector carrying a reporter gene flanked by the AAV TRs. EBV vectors may also be employed to deliver the template, as described above with respect to the rep/cap genes.

In another representative embodiment, the AAV template is provided by a replicating rAAV virus. In still other embodiments, an AAV provirus comprising the AAV template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the AAV rep/cap sequences and the adenovirus helper sequences are supplied by a single adenovirus helper vector. This vector can further comprise the AAV template. The AAV rep/cap sequences and/or the AAV template can be inserted into a deleted region (e.g., the Ela or E3 regions) of the adenovirus.

In a further embodiment, the AAV rep/cap sequences and the adenovirus helper sequences are supplied by a single adenovirus helper vector. According to this embodiment, the AAV template can be provided as a plasmid template.

In another illustrative embodiment, the AAV rep/cap sequences and adenovirus helper sequences are provided by a single adenovirus helper vector, and the AAV template is integrated into the cell as a provirus. Alternatively, the AAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The AAV template can be provided as a separate replicating viral vector. For example, the AAV template can be provided by a AAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by ITRs so that these sequences are not packaged into the AAV virions.

Zhang et al., ((2001) Gene Ther. 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) *Gene Ther.* 6:986 and WO 00/17377).

As a further alternative, the virus vectors of the invention can be produced in insect cells using baculovirus vectors to deliver the rep/cap genes and AAV template as described, for example, by Urabe et al., (2002) Human Gene Ther. 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV. Adenovirus mutants defective for late gene expression are known in the art (e.g., ts100K and ts149 adenovirus mutants).

Methods of Using AGA Vectors

The present invention also relates to methods for delivering an AGA ORF to a cell or a subject to increase production of AGA, e.g., for therapeutic or research purposes in vitro, ex vivo, or in vivo. Thus, one aspect of the invention relates to a method of expressing an AGA open reading frame in a cell, comprising contacting the cell with the polynucleotide, expression cassette, and/or the vector of the invention, thereby expressing the AGA open reading frame in the cell. In some embodiments, the cell is an in vitro cell, an ex vivo cell, or an in vivo cell.

Another aspect of the invention relates to a method of expressing an AGA open reading frame in a subject, comprising delivering to the subject the polynucleotide, expression cassette, vector, and/or transformed cell of the invention, thereby expressing the AGA open reading frame in the subject. In some embodiments, the subject is an animal model of a disorder associated with aberrant AGA gene expression.

A further aspect of the invention relates to a method of treating a disorder associated with aberrant expression of an AGA gene or aberrant activity of an AGA gene product in a subject in need thereof, comprising delivering to the subject a therapeutically effective amount of the polynucleotide, expression cassette, vector, and/or transformed cell of the invention, thereby treating the disorder associated with aberrant expression of the AGA gene in the subject. In some embodiments, the disorder associated with expression of the AGA gene is aspartylglucosaminuria.

In certain embodiments, the polynucleotide, expression cassette, vector, and/or transformed cell is delivered to the subject, e.g., systemically (e.g., intravenously) or directly to the central nervous system (e.g., to the cerebrospinal fluid by intrathecal or intraventricular injection) of the subject. In some embodiments, the polynucleotide, expression cassette, vector, and/or transformed cell is delivered intravenously. In some embodiments, the polynucleotide, expression cassette, vector, and/or transformed cell is delivered intrathecally (IT). IT dose administration is advantageous for the following reasons. First, the IT dose required to achieve the efficacy in preclinical experiments was approximately 10-fold lower compared to IV administration. Second, IT delivery achieves a maximal concentration at dosing in CSF and consequently maximum possible transduction of the CNS, the organ system most afflicted by AGU. Third, IT delivery minimizes the exposure of the immune system to AAV9 vector limiting the virus mostly to CNS space. Fourth is the ability of leaked vector to transduce peripheral organs and express AGA enzyme to reach the deficient non-neuronal tissue via systemic circulation at therapeutic levels. The inability of AGA protein from the systemic circulation to cross the blood brain barrier (BBB) and enter CSF is a limitation of targeting peripheral organs without adequate CNS targeting. IT delivery may be carried out with an injection or by infusion using a pump, e.g., at a rate of about 1 mL per minute.

Recombinant virus vectors according to the present invention find use in both veterinary and medical applications. Suitable subjects include both avians and mammals. The term "avian" as used herein includes, but is not limited to, chickens, ducks, geese, quail, turkeys, pheasant, parrots, parakeets. The term "mammal" as used herein includes, but is not limited to, humans, primates, non-human primates (e.g., monkeys and baboons), cattle, sheep, goats, pigs, horses, cats, dogs, rabbits, rodents (e.g., rats, mice, hamsters, and the like), etc. Human subjects include neonates, infants, juveniles, and adults. Optionally, the subject is "in need of" the methods of the present invention, e.g., because the subject has or is believed at risk for a disorder including those described herein or that would benefit from the delivery of a polynucleotide including those described herein. As a further option, the subject can be a laboratory animal and/or an animal model of disease.

In certain embodiments, the polynucleotide of the invention is administered to a subject in need thereof as early as possible in the life of the subject, e.g., as soon as the subject is diagnosed with aberrant AGA expression or activity. In some embodiments, the polynucleotide is administered to a newborn subject, e.g., after newborn screening has identified aberrant AGA expression or activity. In some embodiments, the polynucleotide is administered to a fetus in utero, e.g., after prenatal screening has identified aberrant AGA expression or activity. In some embodiments, the polynucleotide is administered to a subject as soon as the subject develops symptoms associated with aberrant AGA expression or activity or is suspected or diagnosed as having aberrant AGA expression or activity. In some embodiments, the polynucleotide is administered to a subject before the subject develops symptoms associated with aberrant AGA expression or activity, e.g., a subject that is suspected or diagnosed as having aberrant AGA expression or activity but has not started to exhibit symptoms.

In particular embodiments, the present invention provides a pharmaceutical composition comprising a polynucleotide, expression cassette, vector, and/or transformed cell of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. An exemplary carrier for injection would be saline, e.g., phosphate buffered saline, optionally with additional excipients, e.g., 5% D-sorbitol. For other methods of administration, the carrier may be either solid or liquid. For inhalation administration, the carrier will be respirable, and will preferably be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring an AGA ORF to a cell in vitro. The polynucleotide, expression cassette, and/or vector of the invention may be introduced to the cells in the appropriate amount. The virus vector may be introduced to the cells at the appropriate multiplicity of infection according to standard transduction methods appropriate for the particular target cells. Titers of the virus vector or capsid to administer can vary, depending upon the target cell type and number, and the particular virus vector or capsid, and can be determined by those of skill in the art without undue experimentation. In particular embodiments, at least about $10^3$ infectious units, more preferably at least about $10^5$ infectious units are introduced to the cell.

The cell(s) into which the polynucleotide, expression cassette, and/or vector of the invention, e.g., virus vector, can be introduced may be of any type, including but not limited to neural cells (including cells of the peripheral and central nervous systems, in particular, brain cells such as neurons, oligodendrocytes, glial cells, astrocytes), lung cells, cells of the eye (including retinal cells, retinal pigment epithelium, and corneal cells), epithelial cells (e.g., gut and respiratory epithelial cells), skeletal muscle cells (including myoblasts, myotubes and myofibers), diaphragm muscle cells, dendritic cells, pancreatic cells (including islet cells), hepatic cells, a cell of the gastrointestinal tract (including smooth muscle cells, epithelial cells), heart cells (including cardiomyocytes), bone cells (e.g., bone marrow stem cells), hematopoietic stem cells, spleen cells, keratinocytes, fibroblasts, endothelial cells, prostate cells, joint cells (including, e.g., cartilage, meniscus, synovium and bone marrow), germ cells, and the like. Alternatively, the cell may be any progenitor cell. As a further alternative, the cell can be a stem cell (e.g., neural stem cell, liver stem cell). As still a further alternative, the cell may be a cancer or tumor cell. Moreover, the cells can be from any species of origin, as indicated above.

The polynucleotide, expression cassette, and/or vector of the invention, e.g., virus vector, may be introduced to cells in vitro for the purpose of administering the modified cell to a subject. In particular embodiments, the cells have been removed from a subject, the polynucleotide, expression cassette, and/or vector of the invention, e.g., virus vector, is introduced therein, and the cells are then replaced back into the subject. Methods of removing cells from subject for treatment ex vivo, followed by introduction back into the subject are known in the art (see, e.g., U.S. Pat. No. 5,399,346). Alternatively, the polynucleotide, expression cassette, and/or vector of the invention, e.g., virus vector, is introduced into cells from another subject, into cultured cells, or into cells from any other suitable source, and the cells are administered to a subject in need thereof.

Suitable cells for ex vivo gene therapy are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ or about $10^3$ to about $10^6$ cells will be administered per dose in a pharmaceutically acceptable carrier. In particular embodiments, the cells transduced with the virus vector are administered to the subject in an effective amount in combination with a pharmaceutical carrier.

A further aspect of the invention is a method of administering the polynucleotide, expression cassette, and/or vector of the invention, e.g., virus vector, of the invention to a subject. In particular embodiments, the method comprises a method of delivering an AGA ORF to an animal subject, the method comprising: administering an effective amount of a virus vector according to the invention to an animal subject. Administration of the virus vectors of the present invention to a human subject or an animal in need thereof can be by any means known in the art. Optionally, the virus vector is delivered in an effective dose in a pharmaceutically acceptable carrier.

Dosages of the virus vectors to be administered to a subject will depend upon the mode of administration, the disease or condition to be treated, the individual subject's condition, the particular virus vector, and the nucleic acid to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, or $10^{18}$ transducing units or vector genomes or more, e.g., about $10^7$, $10^8$, $10^9$, $10^{10}$, $10^{11}$, $10^{12}$, $10^{13}$, $10^{14}$, $10^{15}$, or $10^{16}$ transducing units or vector genomes, yet more preferably about $10^{14}$ or $10^{15}$ transducing units or vector genomes.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, topical, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intro-lymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and on the nature of the particular vector that is being used.

In some embodiments, the viral vector is administered to the CNS, the peripheral nervous system, or both.

In some embodiments, the viral vector is administered directly to the CNS, e.g., the brain or the spinal cord. Direct administration can result in high specificity of transduction of CNS cells, e.g., wherein at least 80%, 85%, 90%, 95% or more of the transduced cells are CNS cells. Any method known in the art to administer vectors directly to the CNS can be used. The vector may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and amygdala), limbic system, neocortex, corpus striatum, cerebrum, and inferior colliculus. The vector may also be administered to different regions of the eye such as the retina, cornea or optic nerve. The vector may be delivered into the cerebrospinal fluid (e.g., by lumbar puncture) for more disperse administration of the vector.

The delivery vector may be administered to the desired region(s) of the CNS by any route known in the art, including but not limited to, intrathecal, intracerebral, intraventricular, intranasal, intra-aural, intra-ocular (e.g., intravitreous, sub-retinal, anterior chamber) and peri-ocular (e.g., sub-Tenon's region) delivery or any combination thereof.

The delivery vector may be administered in a manner that produces a more widespread, diffuse transduction of tissues, including the CNS, the peripheral nervous system, and/or other tissues.

Typically, the viral vector will be administered in a liquid formulation by direct injection (e.g., stereotactic injection) to the desired region or compartment in the CNS and/or other tissues. In some embodiments, the vector can be delivered via a reservoir and/or pump. In other embodiments, the vector may be provided by topical application to the desired region or by intra-nasal administration of an aerosol formulation. Administration to the eye or into the ear, may be by topical application of liquid droplets. As a further alternative, the vector may be administered as a solid, slow-release formulation. Controlled release of parvovirus and AAV vectors is described by international patent publication WO 01/91803.

Injectables can be prepared in conventional forms, either as liquid solutions or suspensions, solid forms suitable for solution or suspension in liquid prior to injection, or as emulsions. Alternatively, one may administer the virus vector in a local rather than systemic manner, for example, in a depot or sustained-release formulation. Further, the virus vector can be delivered dried to a surgically implantable matrix such as a bone graft substitute, a suture, a stent, and the like (e.g., as described in U.S. Pat. No. 7,201,898).

Pharmaceutical compositions suitable for oral administration can be presented in discrete units, such as capsules, cachets, lozenges, or tablets, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a virus vector of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sublingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions suitable for parenteral administration can comprise sterile aqueous and non-aqueous injection solutions of the composition of this invention, which preparations are optionally isotonic with the blood of the intended recipient. These preparations can contain antioxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit/dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 μg to about 10 grams of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidyl choline.

Pharmaceutical compositions suitable for rectal administration can be presented as unit dose suppositories. These can be prepared by admixing the composition with one or more conventional solid carriers, such as for example, cocoa butter and then shaping the resulting mixture.

Pharmaceutical compositions of this invention suitable for topical application to the skin can take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharm. Res.* 3:318 (1986)) and typically take the form of an optionally buffered aqueous solution of the composition of this invention. Suitable formulations can comprise citrate or bis\tris buffer (pH 6) or ethanol/water and can contain from 0.1 to 0.2M active ingredient.

The virus vectors disclosed herein may be administered to the lungs of a subject by any suitable means, for example, by administering an aerosol suspension of respirable particles comprised of the virus vectors, which the subject inhales. The respirable particles may be liquid or solid. Aerosols of liquid particles comprising the virus vectors may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors may likewise be produced with any solid particulate medicament aerosol generator, by techniques known in the pharmaceutical art.

Having described the present invention, the same will be explained in greater detail in the following examples, which are included herein for illustration purposes only, and which are not intended to be limiting to the invention.

Example 1

AAV Vectors Comprising Optimized AGA

An AAV vector genome cassette was developed to express the AGA ORF (FIG. 1). This cassette was designed to provide maximal expression from a self-complementary AAV genome that would be packaged within multiple AAV capsids. The cassette consists of, in order: mutant AAV2 ITR, CMV enhancer, chicken beta actin promoter, hybrid/modified MVM intron, codon optimized human AGA ORF, bovine growth hormone polyadenylation site, and wild-type (WT) AAV2 ITR (SEQ ID NO: 7). The human AGA transgene was codon-optimized to impart a significant increase in expression levels. The CBh promoter and BGH polyA are utilized for their ability to drive strong expression within the size limits of a scAAV vector. scAAV vectors are 10-100 times more efficient at transduction compared to traditional AAV vectors.

Figure 2:
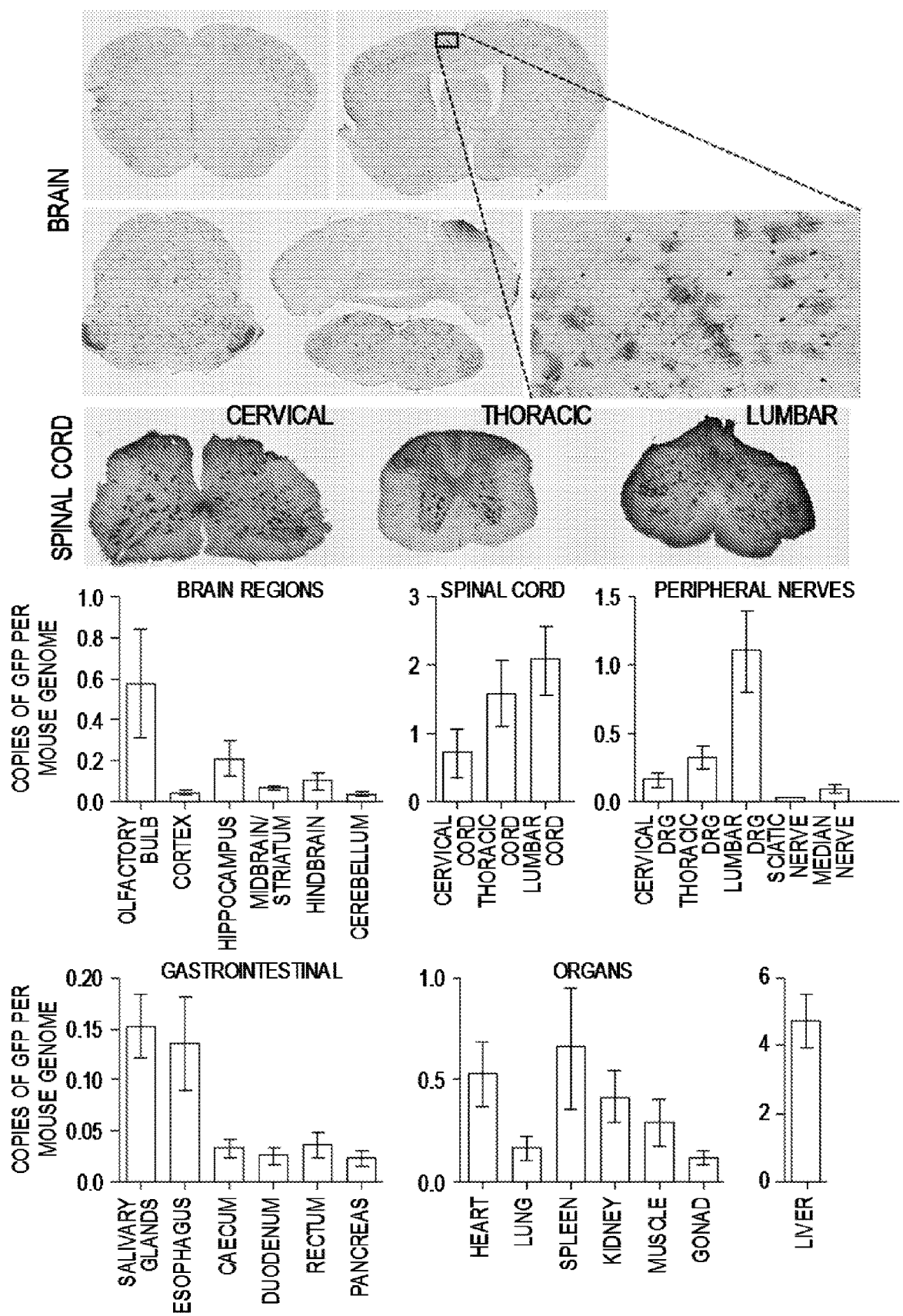
FIG. 2 shows AAV9/GFP biodistribution in WT mice. Eight week-old WT C57BL1/6 mice were given a single lumbar IT injection of scAAV9/CBh-GFP vector at a dose of $4.15 \times 10^{11}$ vg per mouse. At 4 weeks post-injection immunohistochemistry of the brain and spinal cord was conducted to visualize the spatial distribution of GFP expression (top panel; n=4), and qPCR was conducted to quantify the biodistribution of the vector across the nervous system and peripheral tissues (bottom panel; n=5). Bars are the mean, ±SEM.

Before testing the AGA vector, a high-dose intrathecal AAV9 study was conducted in wild-type mice, using a self-complementary AAV9/CBh-GFP reporter vector to study the biodistribution of the vector. This vector construct is identical to AAV9/AGA, except that the GFP gene is inserted in place of the AGA gene. The dose is 1.8-fold higher than the high IT dose of AAV9/AGA tested. The study design is presented Table 4 and the results are provided in FIG. 2.

The study indicated wide-spread biodistribution of transgene delivered via AAV9 vectors across the CNS and to peripheral tissues. The study, while utilizing a different gene than AAV9/AGA, quantified the biodistribution of AAV9 at similar doses as our high dose.

The AGA expression cassette was packaged within an AAV9 capsid for intrathecal injections and the resulting vectors were used to dose AGA knockout mice.

An AGA knock-out (KO) mouse was generated and described in 1996 by Kaartinen et al. (Nat. Med. 2(12):1375 (1996)). The mice have a targeted neomycin cassette insertion in exon 3, which leads to premature termination of the polypeptide at amino acid residue 103. At 5 months old, extensive morphological changes and vacuolization are apparent in the brain and liver. Motor impairment (rotarod) was statistically significant at 20 weeks of age (n=7). Further analysis of the AGU mice indicate the widespread pathology in the brain as early as 5-6 months with extensive loss of cerebellar Purkinje neurons evident by 10 months. The median lifespan was reported to be about 19 months. Terminally ill mice show extensive gliosis in the brain along with pathological changes in the liver and kidney. In 6-month old AGU mice, the MRI findings were reported to be in agreement with human MRI data showing poor differentiation between gray and white matter, and ventricular dilation as confirmed in mice ranging from 6-16 months of age. The KO mouse model does not have detectable AGA activity, and it recapitulates the salient features of the human disease.

The colony maintained by the inventors displayed a disease that was still apparent and consistent with the human phenotype, but disease progression was slower and less severe than that reported by Kaartinen et al. Subtle behavioral deficits emerged after 1 year, no structural changes were visible by MRI at 18 months, and severe ataxia was absent. However, around the age of 20-21 months, a high incidence of extreme urinary retention emerged as a consistent phenotype, which created a pre-defined study endpoint of 18-19 months old for our AGU mice for humanitarian reasons. By histology, severe Purkinje cell loss was evident in the cerebellum at 18-19 months old.

Efficacy studies were designed to test interventions in AGA KO mice before and after emergence of significant CNS pathology (2 vs 6 mo old, respectively). Both IT and IV routes were investigated in parallel for efficacy and safety of AAV9/AGA. Following the studies outlined below, the IT route was chosen for moving forward, partly due to practical translational constraints, i.e., efficacy could be achieved at a lower overall "per subject" vector dose.

Figure 3:
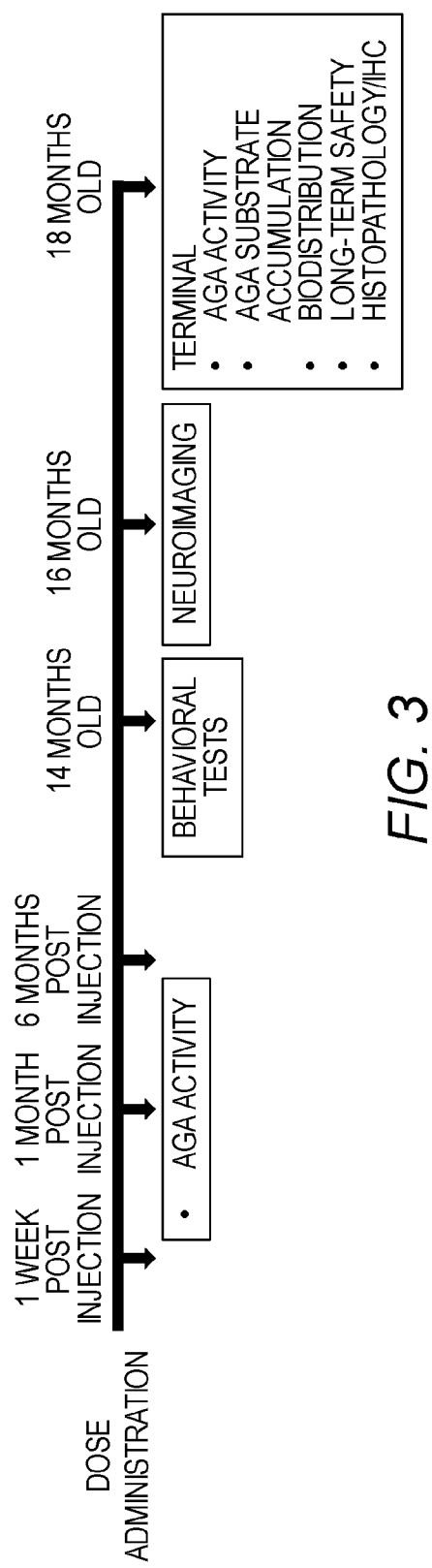
FIG. 3 shows the efficacy study plan, duration and readouts. Doses were administered to the mice aged 2 months (pre-symptomatic) or 6 months (after initiation of degenerative brain pathology). Study readouts at each time point after dose administration or at specified age are listed from left to right.

The study design for efficacy testing is presented in Table 5, as well as FIG. 3. Mice were randomized into treatment cohorts, and the study used approximately equal numbers of males and females. Mice were weighed and assessed for overall body condition monthly. Whenever feasible (in most cases, including all biomarker assessments), study personnel were blinded to the genotype and treatment of the mice, and mice were identified only be generic ID numbers. All mice reaching the planned endpoint of 18-19 months old had specimens collected, with all major tissues either frozen or fixed in formalin. Serum, urine, and CSF were collected from all mice at necropsy. During life, serum and urine were collected pre-injection, then at 0.25, 1, 3, 6, 9 months post-injection. GlcNAc-Asn measurements were conducted in blinded fashion. A subset of samples were assessed in the pilot studies below, but most were archived without testing.

The preclinical mouse studies demonstrated a dose-responsive rescue of disease-specific biomarkers. A summary of the efficacy findings are shown in Table 6.

TABLE 6

| Dose route | Dose level ($\times 10^{10}$ vg) | Conclusions |
| --- | --- | --- |
| Intrathecal | 2 | Increased enzyme activity, reduced the substrate accumulation, but not completely effective at improving behavioral phenotype |
| Intrathecal | 10 | Increased enzyme activity, reduced the substrate accumulation and normalized behavioral phenotype. Note that the IT dose is 10-fold lower compared to the high IV, but the over rescue was comparable. |
| Intravenous | 20 | Increased enzyme activity, reduced the substrate accumulation, but not completely effective at improving behavioral phenotype |
| Intravenous | 100 | Increased enzyme activity, reduced the substrate accumulation and normalized behavioral phenotype |

Figure 4:
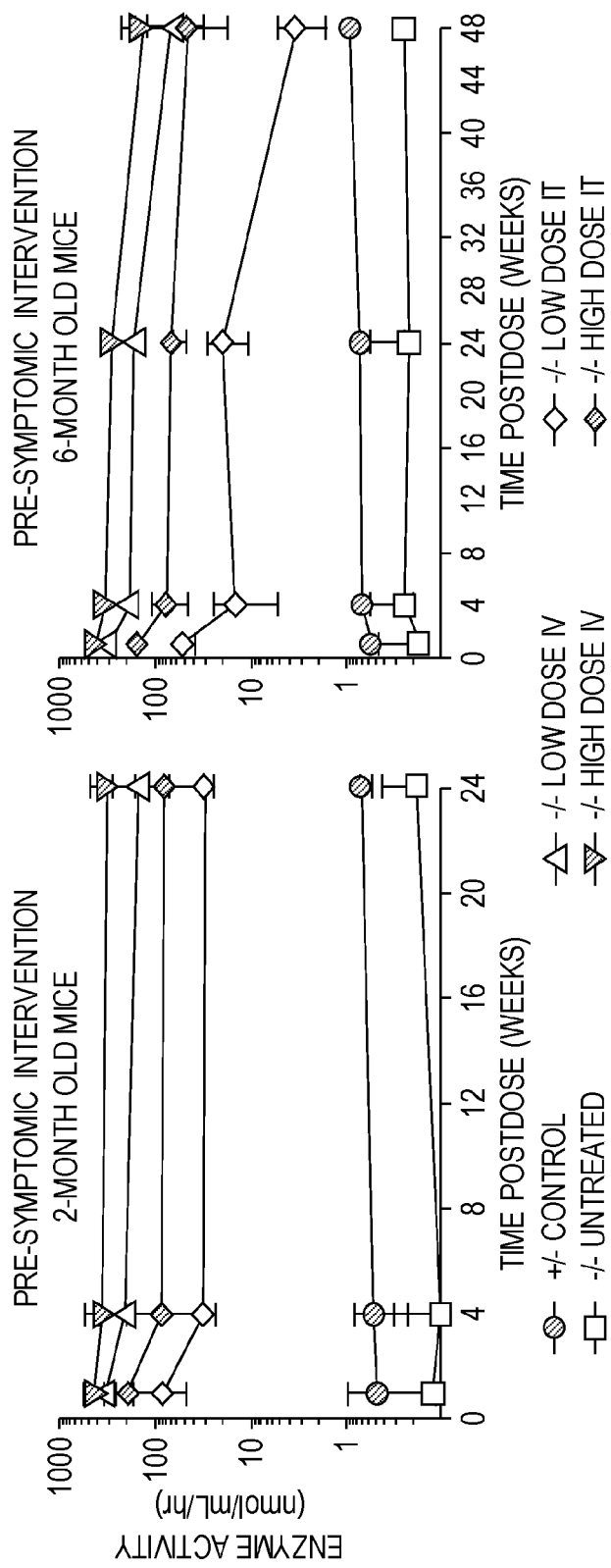
FIG. 4 shows serum AGA activity following AAV9/AGA therapy. Therapy was administered to mice aged 2 months (left; n≥15 per cohort) or 6 months (right; n≥15 per cohort) via IV or IT injection. AGA activity was assayed in serum sampled at 1, 4, 24 and/or 48 weeks following AAV9/AGA therapy. The data are presented as mean±sem, on a logarithmic scale.
Figure 5:
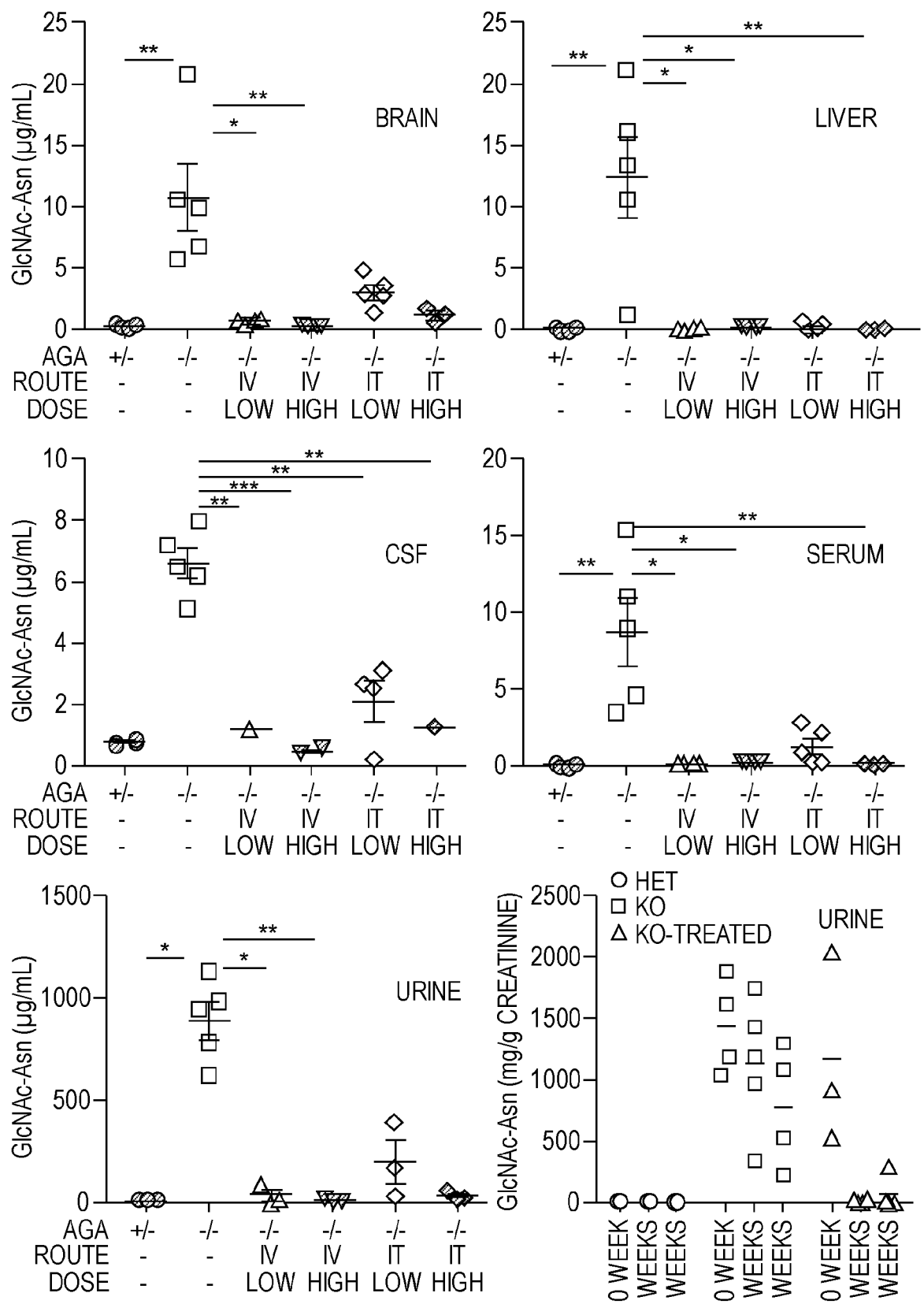
FIG. 5 shows reduced substrate accumulation following AAV9/AGA gene therapy. Six month old mice were treated (IV or IT) and at 18 months of age tissue and body fluid samples were collected. Samples were assayed to quantify the substrate. The data are presented as mean±sem. Untreated AGU+/- and -/- groups were compared using the Mann-Whitney test. Untreated and treated AGU -/- groups were compared by a Kruskal-Wallis with Dunnett's multiple comparison test (*$p<0.005$; $p<0.01$; *$p<0.05$). Lower left panel: Mice at 6 months of age were administered $2 \times 10^{11}$ vg of AAV9/AGA IV. The substrate levels in urine returned to normal by 4 weeks post-injection and are maintained at lower levels (week 8).

Improvements in Biomarkers. Following treatment, several lines of biochemical evidence demonstrated the efficacy of AAV9/AGA in the AGU mouse model. Sustained AGA enzyme levels near or exceeding WT levels were seen in the blood, liver, spinal cord, and brain (blood data shown in FIG. 4). More importantly, dose-responsive normalization of the GlcNAc-Asn (AGA substrate) was seen in urine, serum, CSF, brain, and liver (FIG. 5). To explore neuroimaging biomarkers, a pilot nuclear magnetic resonance study on AGA KO and normal mouse brain lysates identified a

TABLE 4

Biodistribution study design for AAV9 dosed IT in mice

| Genotype | Route* | Age (months) | Sex | Dose ($\times 10^{11}$ vg/ mouse) | Number Dosed | Endpoint |
| --- | --- | --- | --- | --- | --- | --- |
| WT | IT | 2 | F | 4.15 | 9 | 3 months (4 weeks postdose) |

*IT injections were via lumbar puncture, a 5 μL dose in vehicle (350 mM phosphate-buffered saline, 5% sorbitol).

TABLE 5

Proof-of-concept study design for AAV9/AGA therapy.

| Genotype | Route* | Age (months) | Dose ($\times 10^{10}$ vg/ mouse) | Dosed mice | Ongoing mice | Behavior test age (months) | Terminal endpoint |
| --- | --- | --- | --- | --- | --- | --- | --- |
| Het | — | 2 | — | 53 | 53 | 14 | 18 months old |
| KO | — | 2 | — | 65 | 65 | 14 | 18 months old or humane endpoint |
| KO | IT | 2 | 2 | 37 | 37 | 14 | 18 months old or humane endpoint |
| KO | IT | 2 | 10 | 31 | 31 | 14 | 18 months old or humane endpoint |
| KO | IT | 2 | 100 | 15 | 15 | 14 | 18 months old or humane endpoint |
| KO | IV | 2 | 20 | 24 | 24 | 14 | 18 months old or humane endpoint |
| KO | IV | 2 | 100 | 19 | 19 | 14 | 18 months old or humane endpoint |
| Het | — | 6 | — | 31 | 12 | 14 | 18 months old |
| KO | — | 6 | — | 41 | 9 | 14 | 18 months old or humane endpoint |
| KO | IT | 6 | 2 | 18 | 0 | 14 | 18 months old or humane endpoint |
| KO | IT | 6 | 10 | 17 | 0 | 14 | 18 months old or humane endpoint |
| KO | IT | 6 | 100 | 12 | 11 | 14 | 18 months old or humane endpoint |
| KO | IV | 6 | 20 | 15 | 0 | 14 | 18 months old or humane endpoint |
| KO | IV | 6 | 100 | 15 | 0 | 14 | 18 months old or humane endpoint |

Figure 6:
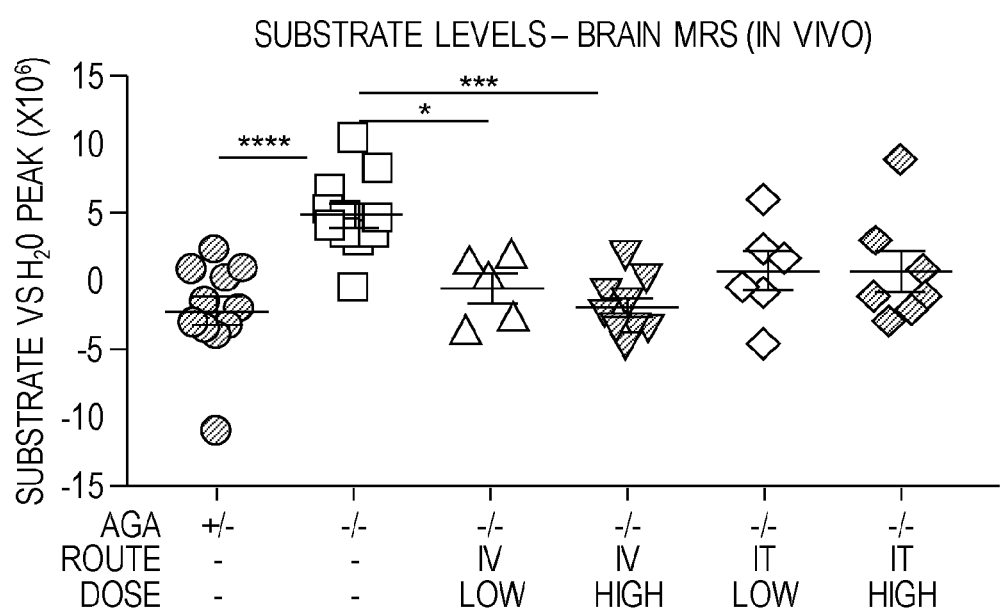
FIG. 6 shows substrate accumulation in brain tissue. Mice received a single dose at 6 months. MRS analysis of brain was performed when mice were 16 month old. The data are presented as mean±sem. Untreated AGU+/- and -/- groups were compared using the Mann-Whitney test. Untreated and treated AGU -/- groups were compared by a Kruskal-Wallis with Dunnett's multiple comparison test (**$p<0.0001$; *$p<0.005$; *$p<0.05$).

*IT injections were via lumbar puncture, a 5 μL dose in vehicle (350 mM phosphate-buffered saline containing 5% sorbitol). IV injections were via the lateral tail vein, a 200 μL dose in vehicle.

disease-specific substrate peak at 5 ppm. MRS was then explored to quantify this peak in live mice, where it was measurable at 5.1 ppm. FIG. 6 shows the quantification of this peak, and its reduction in response to treatment.

Behavioral improvements in KO mice. Improvement in the levels of AGA enzyme and reduction of the AGA substrate in the KO were achieved following AAV9/AGA administration. Based on the pathophysiology of the disease, correction of the underlying insult (substrate accumulation) is expected to halt or slow the neurodegeneration, resulting in a phenotypic rescue. To test this directly, treated mice were evaluated at 14 months old, an age at which the AGU mice show reduced mobility in an open field test.

Patients with AGU tend to withdraw, become calm, lack enthusiasm and sit quietly for hours as the disease progresses. Open field exploration test in mice is a tool to assess novel environment exploration, anxiety-related behavior and general locomotor activity. The exploratory locomotor activity in the first 5-minutes of the test session sufficiently captures the critical aspects of anxiety-related behavior. In this experimental design, heterozygous (normal) littermate mice were tested in parallel as reference controls. At 6 months old, AGA KO mice were randomized into one of 5 groups: 1) untreated, 2) IV high dose, 3) IV low dose, 4) IT high dose, and 5) IT low dose. This age is significant, since neuropathology is present in the mice at this age. At approximately 8 months post-injection (14 months old), all mice were assayed for their mobility with the open field test. Distance travelled, high mobility time, and immobility time were quantified by an automated Noldus video tracking system. These tests reflect the activity and anxiety in the treated and untreated KO mice.

Figure 7:
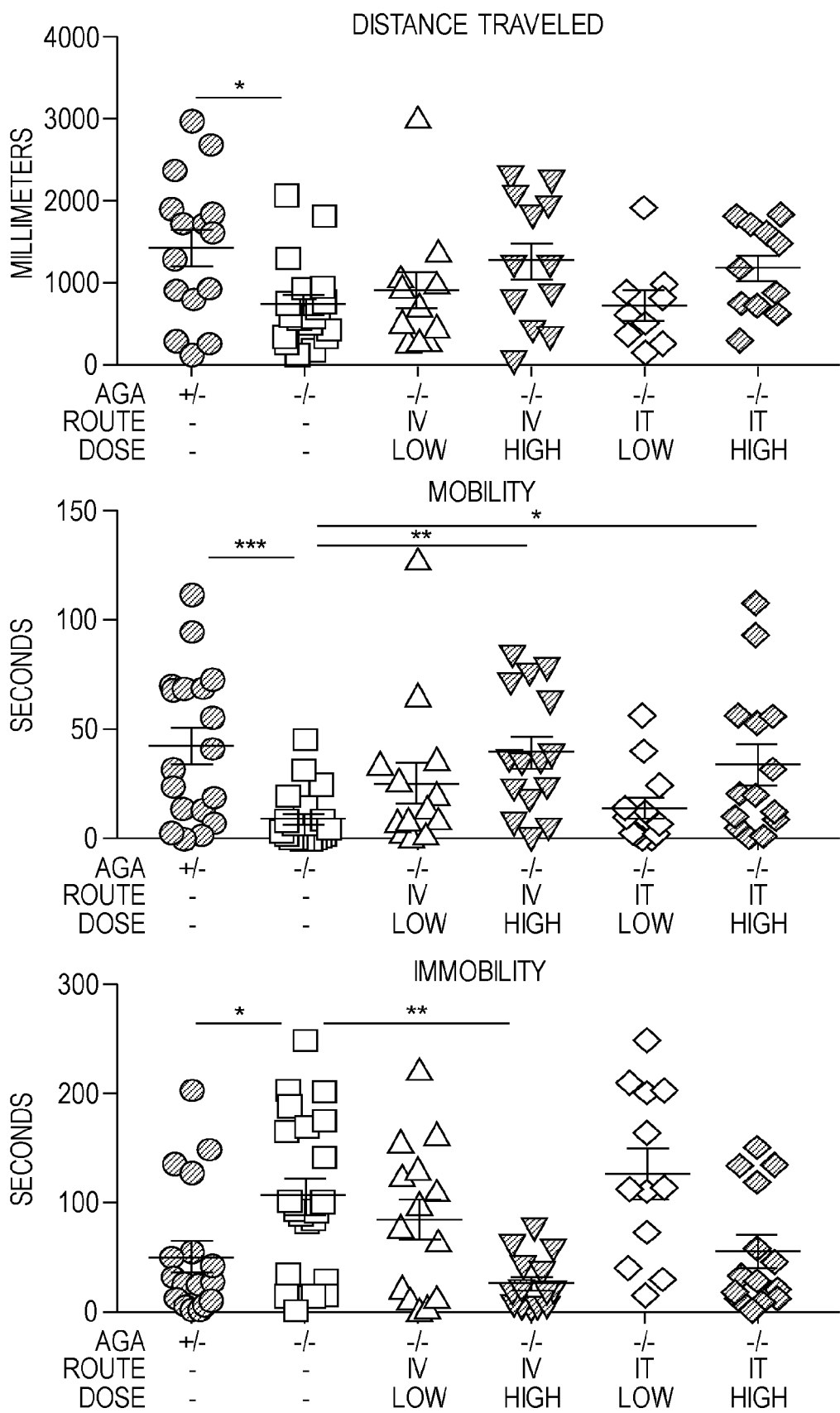
FIG. 7 shows high dose treatments with AAV9/AGA rescues mobility. Mice received a single dose at 6 months and the test was administered at 14 months of age. The mice were allowed to survey an open field. The distance traveled in the first 5 minutes (top panel), time spent moving around (mobility, bottom left) and time spent still (immobility, bottom right) were recorded and quantified by automated Noldus video tracking system. The data are presented as mean±sem. Mann-Whitney test compared untreated AGU+/- to -/- group. Untreated and treated AGU -/- groups were compared by One-way ANOVA followed by Dunn's multiple comparison test (*$p<0.005$; $p<0.01$; *$p<0.05$).

Altogether, there was a high degree of variability in all groups which may be explained by the mixed genetic background of the mice and the old age of testing. The heterozygous mice were highly mobile, inspecting the new/unfamiliar surroundings, and they spent less time immobile/stationary displaying higher levels of anxiety and activity (FIG. 7). The untreated KO mice displayed lower exploratory behavior and mobility relative to heterozygotes. The treated KO mice showed improvement in their mobility compared to the untreated cohorts. Cohorts treated with higher dose levels spent significantly more time mobile, although the distances traveled during this period were not significantly different from untreated mice. It should be noted that the treatment was initiated in mice that were 6 months old, an age when significant brain pathology and degeneration is present. Studies in mice injected at 2 months old are ongoing. We interpret these results as showing a significant behavioral normalization of mice treated after the onset of disease pathology, by either IV or IT administration of AAV9/AGA, at the high dose. This is a pivotal result in that it demonstrates a clear phenotypic benefit to the AGU mice, and it defines a minimally effective dose since the low dose was unable to fully rescue the disease phenotype.

Figure 8:
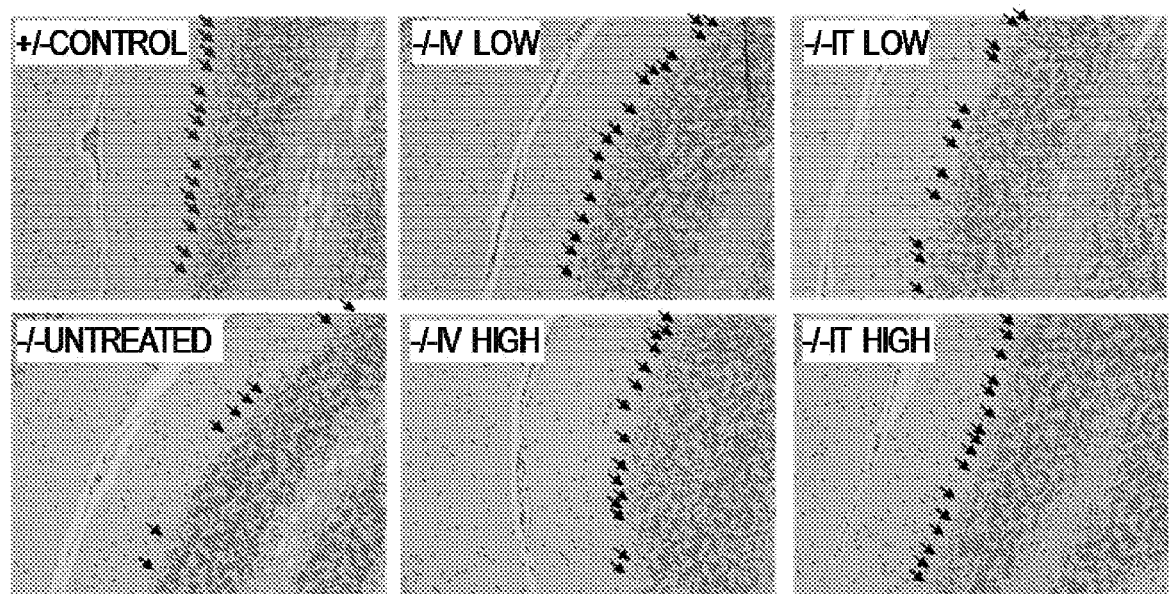
FIG. 8 shows gene therapy preserves Purkinje cell populations. AGU KO mice received a single AAV9/AGA dose at 6 months and brain from the mice was collected at 18 months of age. Fixed brain tissue sectioned at 5μ thick was stained with hematoxylin and eosin (top panel). Purkinje cells (arrow) are identified in representative pictures from each cohort. Purkinje cells were quantified for each cohort (bottom panel). The data are presented as mean±sem. Mann-Whitney test compared untreated AGU+/- to -/- group. Untreated and treated AGU -/- groups were compared by One-way ANOVA followed by Dunn's multiple comparison test(**$p<0.01$; *$p<0.05$).
Figure 8:
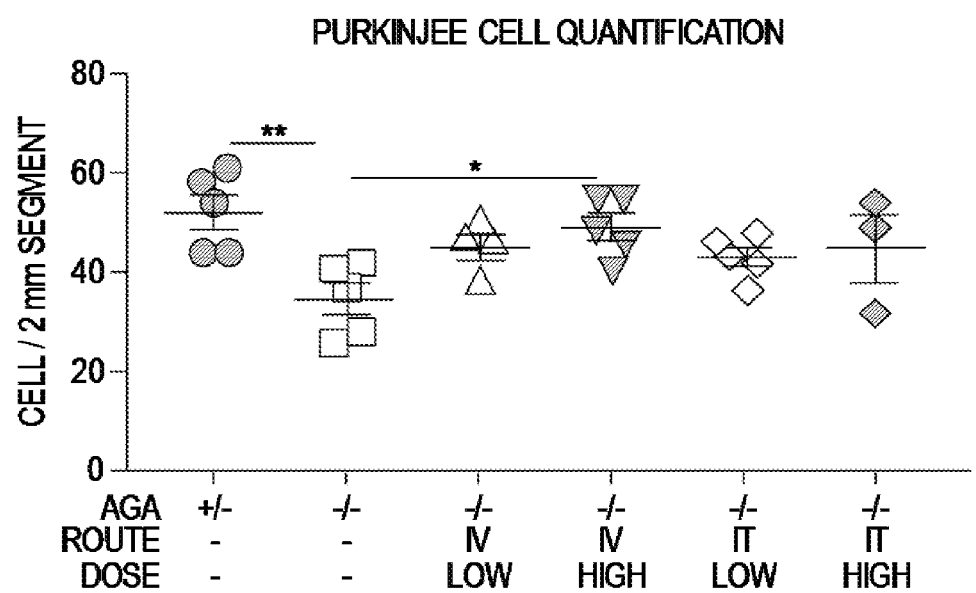

AGU Histopathology. Lysosomal hypertrophy, as evidenced by cellular vacuolation, in visceral organs of the KO mice resembles human AGU histopathology. Neuronal, glial and endothelial cells of the frontal cortex, cerebellum, brain stem and spinal cord of the AGU mice are vacuolated around 6 months and progressively worsens. In KO mice over 18 months of age, a reported 70-80% of Purkinje cells in cerebellar cortex are lost compared to age-matched controls. In our studies, untreated AGU mice showed less severe but still significant loss of Purkinje cells compared to controls (FIG. 8). Purkinje cells were preserved in significantly larger number at higher dose in symptomatic AGU mice dosed at 6 months of age.

Pilot non-GLP safety studies indicate a favorable safety margin for AAV9/AGA. Compared to their wild-type litter mates, the AGU KO were reported to have poor survival, with only 8 of 20 making it past the 20 month mark. We have seen mostly normal lifespan of untreated AGU mice up to 20 months, and we are not using survival as an efficacy outcome measure. We initiated an additional cohort (in progress at 11 mo post-injection, n=27), wherein the AGU mice received a higher "10× dose" (IT, $1\times10^{12}$ vg) above the minimally-effective $1\times10^{11}$ vg dose. Thus far, no signs of morbidity have been seen compared to normal or untreated AGU mice. While we noted one unexplained death in a treated AGU mouse, there were three unexplained deaths in a parallel cohort of vehicle-injected AGU mice. Subtle toxic effects are not ruled out, but our data suggest a favorable long-term safety profile of AAV9/AGA.

Example 2

Improved Processing and Activity of Optimized AGA

Figure 9E:
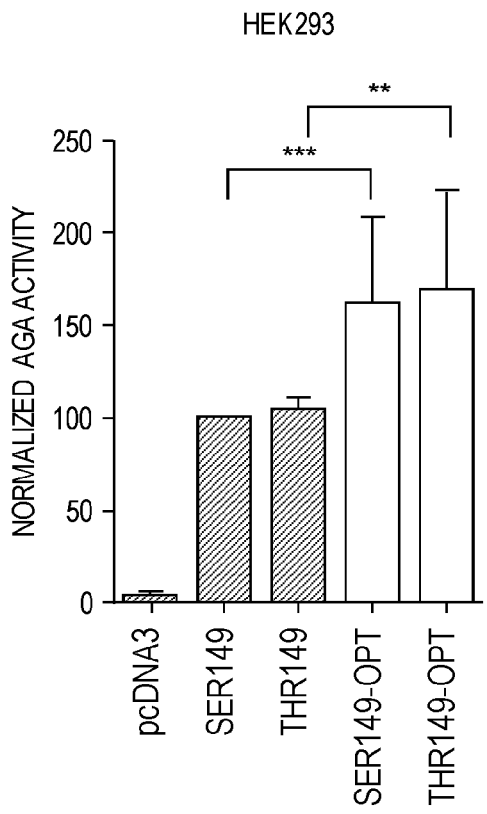
Figure 9F:
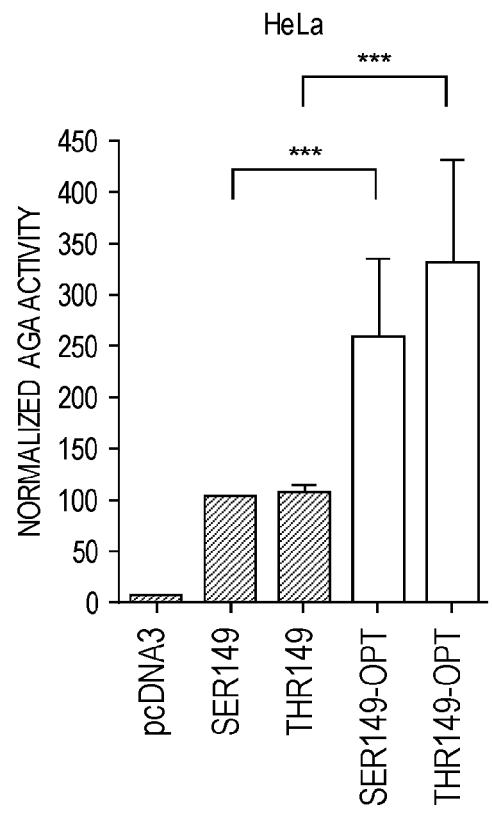
Figure 9G:
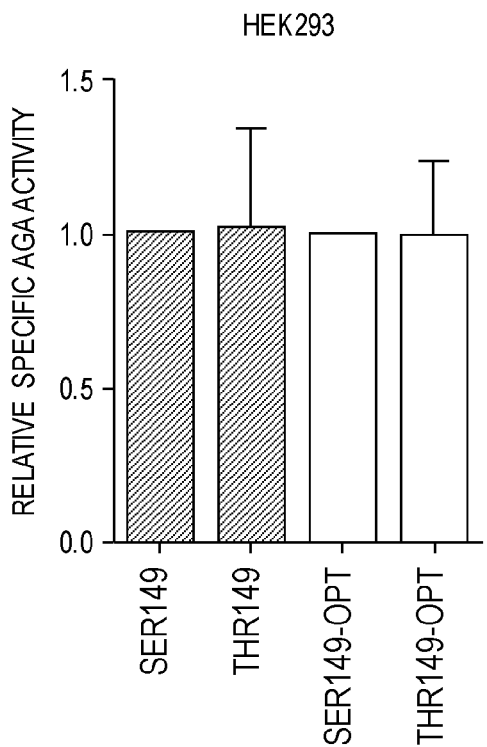
Figure 9H:
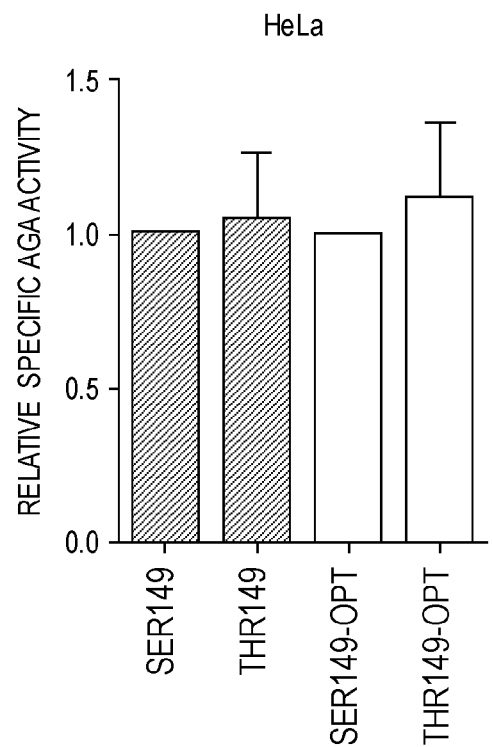

In order to use AGA for gene therapy, it is important to obtain a high level of enzyme expression acid activity in target tissues. To this end, the human AGA gene was optimized for code usage. The optimized sequence encoding either Ser 149 or Thr149 (two naturally occurring human variants) were cloned into the pcDNA3 expression vector. The expression and activity of the optimized variants were compared with constructs exhibiting the normal human cDNA sequence. A significantly higher proteins expression was obtained in HEK and HeLa cells of the codon optimized variants, as compared to the respective non-optimized ones (FIGS. 9A-9D). Consistently, the normalized enzyme activities were significantly higher with the optimized AGA variants (FIGS. 9E-9F). The optimized Thr149 AGA showed a tendency to higher expression and activity than the Ser149 counterpart, but this difference was not significant. The relative specific activities of Ser149 and Thr149 AGA were not significantly different from each other (FIGS. 9G-9H).

The foregoing is illustrative of the present invention, and is not to be construed as limiting thereof. The invention is defined by the following claims, with equivalents of the claims to be included therein.

That which is claimed is:

1. A polynucleotide comprising a human AGA open reading frame, wherein the nucleotide sequence has been codon-optimized for expression in human cells, wherein said polynucleotide comprises the nucleotide sequence of SEQ ID NO:1 or a sequence at least about 90% identical thereto.

2. An expression cassette comprising the polynucleotide of claim 1.

3. The expression cassette of claim 2, wherein the polynucleotide is operably linked to a promoter.

4. The expression cassette of claim 2, wherein the polynucleotide is operably linked to an enhancer.

5. The expression cassette of claim 2, wherein the polynucleotide is operably linked to an intron.

6. The expression cassette of claim 2, wherein the polynucleotide is operably linked to a polyadenylation signal.

7. The expression cassette of claim 2, further comprising at least one adeno-associated virus (AAV) inverted terminal repeat (ITR).

8. The expression cassette of claim 2, wherein the expression cassette is a self-complementary AAV genome.

9. The expression cassette of claim 2, wherein the expression cassette comprises, in 5' to 3' direction, an enhancer, a promoter, an intron, a human AGA open reading frame, and a polyadenylation site.

10. The expression cassette of claim 9, wherein the expression cassette comprises an AAV ITR, an enhancer, a promoter, an intron, a human AGA open reading frame, a polyadenylation site, and an AAV ITR.

11. The expression cassette of claim 10, wherein the expression cassette comprises, in 5' to 3' direction, a mutant AAV ITR, a CMV enhancer, a chicken beta actin promoter, a hybrid/modified MVM intron, a human AGA open reading frame, a bovine growth hormone polyadenylation site, and a wild-type AAV ITR.

12. The expression cassette of claim 11, comprising the nucleotide sequence of SEQ ID NO:7 or a sequence at least about 90% identical thereto.

13. A vector comprising the polynucleotide of claim 1, such as a viral vector.

14. The vector of claim 13, wherein the vector is an AAV vector.

15. The vector of claim 14, wherein the AAV vector comprises wild-type capsid proteins.

16. The vector of claim 14, wherein the AAV vector comprises a modified capsid protein with altered tropism compared to a wild-type capsid protein.

17. An isolated transformed cell comprising the polynucleotide of claim 1.

18. A pharmaceutical formulation comprising the polynucleotide of claim 1 in a pharmaceutically acceptable carrier.

19. A method of treating a disorder associated with aberrant expression of an AGA gene or aberrant activity of an AGA gene product in a subject in need thereof, comprising delivering to the subject a therapeutically effective amount of the polynucleotide of claim 1, thereby treating the disorder associated with aberrant expression of the AGA gene in the subject or aberrant activity of the AGA gene product.

* * * * *

UNITED STATES PATENT AND TRADEMARK OFFICE
CERTIFICATE OF CORRECTION

PATENT NO. : 11,491,241 B2
APPLICATION NO. : 16/761290
DATED : November 8, 2022
INVENTOR(S) : Steven James Gray It is certified that error appears in the above-identified patent and that said Letters Patent is hereby corrected as shown below:

In the Claims

Column 39, Lines 4-5, Claim 13: Please correct "claim 1, such as a viral vector." to read --claim 1.--

Signed and Sealed this
Fourteenth Day of March, 2023

Katherine Kelly Vidal
*Director of the United States Patent and Trademark Office*

SEQUENCE LISTING

```
<160> NUMBER OF SEQ ID NOS: 7

<210> SEQ ID NO 1
<211> LENGTH: 1044
<212> TYPE: DNA
<213> ORGANISM: Artificial
<220> FEATURE:
```

<223> OTHER INFORMATION: Human codon-optimized AGA open reading frame

<400> SEQUENCE: 1

```
atggcacgca agtcaaacct ccccgtcctg ctggtgcctt tcctgctgtg ccaagcactg      60
gtccggtgct cctcaccgct gccccttgtg gtgaacacct ggcccttcaa gaatgctacc     120
gaggcagcat ggagggctct tgcatcaggc ggttccgccc tggatgccgt ggagagcgga     180
tgtgctatgt gtgaacgcga acaatgcgac ggatcagtgg gattcggcgg atcacctgac     240
gagctcgggg aaactactct tgacgccatg attatggacg aactaccat ggacgtgggt      300
gccgtgggcg atctccgccg cattaagaac gccattggag tggcccggaa ggtgcttgaa     360
cacaccaccc ataccctcct cgtcggagag tctgctacta ccttcgctca gtctatgggg     420
tttatcaatg aggatctgag caccaccgca tctcaggctc tccactcaga ctggctggcc     480
cgcaactgcc aaccgaacta ctggaggaat gtcatccctg atccatccaa gtattgcgga     540
ccttacaagc caccagggat tctgaaacag acatcccca tccataaaga aaccgaggac      600
gaccggggac atgacactat cggaatggtg gtgatccata agaccgggca catcgccgct     660
ggaaccagca ccaatgggat caaattcaaa attcatggta gagtcggaga tagcccgatt     720
cctggtgctg gggcctacgc tgacgacact gccggagctg ccgcagctac cgggaatgga     780
gacatcctta tgaggttcct gcccctcata caagccgtgg aatacatgcg agaggcgag      840
gacccaacca ttgcctgtca aaggtgatc agccggattc agaagcactt ccccgagttc      900
ttcggtgccg tcatctgtgc aaacgtgact ggttcctacg gtgccgcctg caataagctt     960
agcaccttca ctcagttttc tttatggtg tataactctg aaaagaacca gccaaccgag     1020
gagaaggtcg attgcatcta atga                                            1044
```

<210> SEQ ID NO 2
<211> LENGTH: 306
<212> TYPE: DNA
<213> ORGANISM: Artificial
<220> FEATURE:
<223> OTHER INFORMATION: Chicken beta-actin promoter

<400> SEQUENCE: 2

```
tacgtattag tcatcgctat taccatggtc gaggtgagcc ccacgttctg cttcactctc      60
cccatctccc cccctccc accccaatt ttgtatttat ttattttta attattttgt         120
gcagcgatgg gggcgggggg ggggggggg cgcgcgccag gcggggcggg gcggggcgag      180
gggcggggcg gggcgaggcg gagaggtgcg gcggcagcca atcagagcgg cgcgctccga     240
aagtttcctt ttatggcgag gcggcggcgg cggcggccct ataaaaagcg aagcgcgcgg     300
cgggcg                                                                306
```

<210> SEQ ID NO 3
<211> LENGTH: 137
<212> TYPE: DNA
<213> ORGANISM: Artificial
<220> FEATURE:
<223> OTHER INFORMATION: Chicken beta-actin exon 1 and intron 1

<400> SEQUENCE: 3

```
ggagtcgctg cgacgctgcc ttcgccccgt gccccgctcc gccgccgcct cgcgccgccc      60
gccccggctc tgactgaccg cgttactccc acaggtgagc gggcgggacg gcccttctcc     120
tccgggctgt aattagc                                                    137
```

```
<210> SEQ ID NO 4
<211> LENGTH: 256
<212> TYPE: DNA
<213> ORGANISM: Artificial
<220> FEATURE:
<223> OTHER INFORMATION: Cytomegalovirus enhancer

<400> SEQUENCE: 4
tacataactt acggtaaatg gcccgcctgg ctgaccgccc aacgacccccc gcccattgac      60 gtcaatagta acgccaatag ggactttcca ttgacgtcaa tgggtggagt atttacggta     120
aactgcccac ttggcagtac atcaagtgta tcatatgcca agtacgcccc ctattgacgt     180
caatgacggt aaatggcccg cctggcattg tgcccagtac atgaccttat gggactttcc     240
tacttggcag tacatc                                                     256

<210> SEQ ID NO 5
<211> LENGTH: 92
<212> TYPE: DNA
<213> ORGANISM: Artificial
<220> FEATURE:
<223> OTHER INFORMATION: Hybrid/modified MVM intron

<400> SEQUENCE: 5
aagaggtaag ggtttaaggg atggttggtt ggtggggtat taatgtttaa ttacctggag      60
cacctgcctg aaatcacttt ttttcaggtt gg                                    92

<210> SEQ ID NO 6
<211> LENGTH: 254
<212> TYPE: DNA
<213> ORGANISM: Artificial
<220> FEATURE:
<223> OTHER INFORMATION: Bovine growth hormone polyadenylation signal

<400> SEQUENCE: 6
ctcgactgtg ccttctagtt gccagccatc tgttgtttgc ccctcccccg tgccttcctt      60
gaccctggaa ggtgccactc ccactgtcct ttcctaataa aatgaggaaa ttgcatcgca     120
ttgtctgagt aggtgtcatt ctattctggg gggtggggtg gggcaggaca gcaaggggga     180
ggattgggaa gacaacagca ggcatgctgg ggatgcggtg ggctctatgg cttctgaggc     240
ggaaagaacc agct                                                       254

<210> SEQ ID NO 7
<211> LENGTH: 2123
<212> TYPE: DNA
<213> ORGANISM: Artificial
<220> FEATURE:
<223> OTHER INFORMATION: AGA expression cassette

<400> SEQUENCE: 7
tacataactt acggtaaatg gcccgcctgg ctgaccgccc aacgacccccc gcccattgac      60 gtcaatagta acgccaatag ggactttcca ttgacgtcaa tgggtggagt atttacggta     120
aactgcccac ttggcagtac atcaagtgta tcatatgcca agtacgcccc ctattgacgt     180
caatgacggt aaatggcccg cctggcattg tgcccagtac atgaccttat gggactttcc     240
tacttggcag tacatctacg tattagtcat cgctattacc atggtcgagg tgagccccac     300
gttctgcttc actctcccca tctccccccc ctccccaccc ccaattttgt atttatttat     360
tttttaatta ttttgtgcag cgatggggggg gggggggggg ggggggcgcg cgccaggcgg     420
ggcggggcgg ggcgaggggc ggggcggggc gaggcggaga ggtgcggcgg cagccaatca     480
```

```
gagcggcgcg ctccgaaagt ttccttttat ggcgaggcgg cggcggcggc ggccctataa      540
aaagcgaagc gcgcggcggg cgggagtcgc tgcgacgctg ccttcgcccc gtgccccgct      600
ccgccgccgc ctcgcgccgc ccgccccggc tctgactgac cgcgttactc ccacaggtga      660
gcgggcggga cggcccttct cctccgggct gtaattagct gagcaagagg taagggttta      720
agggatggtt ggttggtggg gtattaatgt ttaattacct ggagcacctg cctgaaatca      780 cttttttttca ggttggaccg gtcgccacca tggcacgcaa gtcaaacctc ccgtcctgc      840 tggtgccttt cctgctgtgc caagcactgg tccggtgctc ctcaccgctg ccccttgtgg      900
tgaacacctg gcccttcaag aatgctaccg aggcagcatg gagggctctt gcatcaggcg      960
gttccgccct ggatgccgtg gagagcggat gtgctatgtg tgaacgcgaa caatgcgacg     1020
gatcagtggg attcggcgga tcacctgacg agctcgggga aactactctt gacgccatga     1080
ttatggacgg aactaccatg gacgtgggtg ccgtgggcga tctccgccgc attaagaacg     1140
ccattggagt ggcccggaag gtgcttgaac acaccaccca taccctcctc gtcggagagt     1200
ctgctactac cttcgctcag tctatggggt ttatcaatga ggatctgagc accaccgcat     1260
ctcaggctct ccactcagac tggctggccc gcaactgcca accgaactac tggaggaatg     1320
tcatccctga tccatccaag tattgcggac cttacaagcc accagggatt ctgaaacagg     1380
acatccccat ccataaagaa accgaggacg accggggaca tgacactatc ggaatggtgg     1440
tgatccataa gaccgggcac atcgccgctg aaccagcac caatgggatc aaattcaaaa     1500
ttcatggtag agtcggagat agcccgattc ctggtgctgg ggcctacgct gacgacactg     1560
ccggagctgc cgcagctacc gggaatggag acatccttat gaggttcctg ccctcatacc     1620
aagccgtgga atacatgcgg agaggcgagg acccaaccat tgcctgtcag aaggtgatca     1680
gccggattca gaagcacttc cccgagttct tcggtgccgt catctgtgca aacgtgactg     1740
gttcctacgg tgccgcctgc aataagctta gcaccttcac tcagtttttct tttatggtgt     1800 ataactctga aaagaaccag ccaaccgagg agaaggtcga ttgcatctaa tgagcggccg     1860
cggggatccc tcgactgtgc cttctagttg ccagccatct gttgtttgcc cctcccccgt     1920
gccttccttg accctggaag gtgccactcc cactgtcctt tcctaataaa atgaggaaat     1980
tgcatcgcat tgtctgagta ggtgtcattc tattctgggg ggtggggtgg ggcaggacag     2040 caaggggag gattgggaag acaacagcag gcatgctggg gatgcggtgg gctctatggc     2100
ttctgaggcg gaaagaacca gct                                              2123
```